(12) United States Patent
Dumousseaux

(10) Patent No.: US 7,981,404 B2
(45) Date of Patent: *Jul. 19, 2011

(54) COMPOSITION FOR APPLICATION TO THE SKIN, TO THE LIPS, TO THE NAILS, AND/OR TO HAIR

(75) Inventor: Christophe Dumousseaux, Tokyo (JP)

(73) Assignee: L'Oreal S.A., Paris (FR)

( * ) Notice: Subject to any disclaimer, the term of this patent is extended or adjusted under 35 U.S.C. 154(b) by 1266 days.

This patent is subject to a terminal disclaimer.

(21) Appl. No.: 11/100,513

(22) Filed: Apr. 7, 2005

(65) Prior Publication Data

US 2005/0257335 A1 Nov. 24, 2005

Related U.S. Application Data

(60) Provisional application No. 60/564,971, filed on Apr. 26, 2004.

(30) Foreign Application Priority Data

Apr. 8, 2004 (FR) ..................................... 04 50712

(51) Int. Cl.
*A61K 8/00* (2006.01)

(52) U.S. Cl. ............................................ 424/63; 424/69

(58) Field of Classification Search ........................ None
See application file for complete search history.

(56) References Cited

U.S. PATENT DOCUMENTS

| | | | |
|---|---|---|---|
| 3,030,967 A | 4/1962 | Peyron | |
| 3,516,422 A | 6/1970 | Bechtold et al. | |
| 3,836,537 A | 9/1974 | Boerwinkle et al. | |
| 3,910,862 A | 10/1975 | Barabas et al. | |
| 3,926,659 A | 12/1975 | Bernhard et al. | |
| 3,937,811 A | 2/1976 | Papantoniou et al. | |
| 4,031,307 A | 6/1977 | DeMartino et al. | |
| 4,055,377 A | 10/1977 | Erickson et al. | |
| 4,131,576 A | 12/1978 | Iovine et al. | |
| 4,223,009 A | 9/1980 | Chakrabarti | |
| 4,318,844 A | 3/1982 | Kohler et al. | |
| 4,693,935 A | 9/1987 | Mazurek | |
| 4,728,571 A | 3/1988 | Clemens et al. | |
| 4,972,037 A | 11/1990 | Garbe et al. | |
| 4,981,902 A | 1/1991 | Mitra et al. | |
| 4,981,903 A | 1/1991 | Garbe et al. | |
| 5,030,669 A * | 7/1991 | Hendrickson et al. ........ 523/333 | |
| 5,040,914 A | 8/1991 | Fitjer | |
| 5,061,481 A | 10/1991 | Suzuki et al. | |
| 5,066,485 A | 11/1991 | Brieva et al. | |
| 5,122,418 A | 6/1992 | Nakane et al. | |
| 5,133,805 A | 7/1992 | Kurata et al. | |
| 5,162,410 A | 11/1992 | Sweet | |
| 5,188,899 A | 2/1993 | Matsumoto et al. | |
| 5,199,808 A | 4/1993 | Gueret | |
| 5,209,924 A | 5/1993 | Garbe et al. | |
| 5,219,560 A | 6/1993 | Suzuki et al. | |
| 5,316,026 A | 5/1994 | Jenkins | |
| 5,330,747 A | 7/1994 | Krzysik | |
| 5,356,617 A * | 10/1994 | Schlossman ..................... 424/63 |
| 5,362,485 A | 11/1994 | Hayama et al. | |
| 5,380,359 A | 1/1995 | Honda et al. | |
| 5,424,006 A | 6/1995 | Murayama et al. | |
| 5,451,610 A | 9/1995 | Krzysik | |
| 5,468,477 A | 11/1995 | Kumar et al. | |
| 5,472,798 A | 12/1995 | Kumazawa et al. | |
| 5,486,354 A | 1/1996 | Defossez et al. | |
| 5,512,273 A | 4/1996 | Martin | |
| 5,562,706 A | 10/1996 | Lauterbach et al. | |
| 5,625,005 A | 4/1997 | Mallya et al. | |
| 5,641,835 A | 6/1997 | Smith et al. | |
| 5,643,672 A | 7/1997 | Marchi et al. | |
| 5,658,574 A | 8/1997 | Bahary et al. | |
| 5,683,706 A | 11/1997 | LaFleur et al. | |
| 5,725,882 A | 3/1998 | Kumar et al. | |
| 5,846,310 A | 12/1998 | Noguchi et al. | |
| 5,849,275 A | 12/1998 | Calello et al. | |
| 5,849,318 A | 12/1998 | Imai et al. | |
| 5,851,517 A | 12/1998 | Mougin et al. | |
| 5,856,653 A | 1/1999 | Boudreaux | |
| 5,873,375 A | 2/1999 | Johnson et al. | |
| 5,874,069 A | 2/1999 | Mendolia et al. | |

(Continued)

FOREIGN PATENT DOCUMENTS

DE 102 19 196 11/2003

(Continued)

OTHER PUBLICATIONS

Minolta, Precise Color Communications, 1998, of record.*
Minolta, Precise Color Communication, 1998.*
Precise Color Communications (Minolta, 1998).*
English language Abstract of JP 11-181329, Jul. 6, 1999.
English language Abstract of JP 2003-000338, Jan. 7, 2003.
English language Abstract of JP 2004-043367, Feb. 12, 2004.
English language Abstract of JP 2004-123681, Apr. 22, 2004.
English language Abstract of JP 2004-307424, Nov. 4, 2004.
English language Abstract of JP 61-112008, May 30, 1986.
English language Abstract of JP 7-316015, Dec. 5, 1995.
"Precise Color Communication", Konica Minolta Sensing, Inc. (1998).
Japanese Publication S55-81809, Kiyoshi Inoue, Method of Magnatized Cosmetic Agent Usage, Jun. 20, 1980.
Office Action mailed Jan. 15, 2009, in co-pending U.S. Appl. No. 11/100,514.
Office Action mailed Jan. 22, 2009, in co-pending U.S. Appl. No. 11/101,400.
Office Action mailed Jan. 27, 2009, in co-pending U.S. Appl. No. 11/770,177.
Office Action mailed Jan. 7, 2009, in co-pending U.S. Appl. No. 11/100,566.

(Continued)

*Primary Examiner* — Anand U Desai
*Assistant Examiner* — Melissa S Mercier
(74) *Attorney, Agent, or Firm* — Finnegan, Henderson, Farabow, Garrett & Dunner LLP

(57) ABSTRACT

A composition for application to the skin, the lips, the nails, and/or hair is disclosed, wherein the composition comprises at least one first coloring agent in an amount sufficient to color the composition, comprising particles of at least one composite pigment, the particles comprising an inorganic core at least partially coated with at least one organic coloring substance, and at least one second coloring agent in an amount sufficient to produce a specific optical effect in the composition which is visibly perceptible to a human observer. A method of making up the skin, lips, nails, and/or hair is also disclosed.

72 Claims, No Drawings

U.S. PATENT DOCUMENTS

| | | | |
|---|---|---|---|
| 5,919,441 A | 7/1999 | Mendolia et al. | |
| 5,931,166 A | 8/1999 | Weber et al. | |
| 5,948,393 A | 9/1999 | Tomomasa et al. | |
| 5,954,871 A | 9/1999 | Nicolas-Morgantini et al. | |
| 5,981,680 A | 11/1999 | Petroff et al. | |
| 6,001,338 A | 12/1999 | Mondet | |
| 6,033,650 A | 3/2000 | Calello et al. | |
| 6,051,216 A | 4/2000 | Barr et al. | |
| 6,071,632 A | 6/2000 | Hall-Goulle | |
| 6,074,654 A | 6/2000 | Dreschler et al. | |
| 6,117,435 A | 9/2000 | Painter et al. | |
| 6,117,574 A | 9/2000 | Watanabe et al. | |
| 6,177,093 B1 | 1/2001 | Lombardi et al. | |
| 6,203,781 B1 | 3/2001 | Chevalier et al. | |
| 6,209,548 B1 | 4/2001 | Harrison et al. | |
| 6,280,655 B1 | 8/2001 | Xu et al. | |
| 6,299,979 B1 | 10/2001 | Neubauer et al. | |
| 6,358,495 B1 | 3/2002 | Nishihama et al. | |
| 6,387,498 B1 | 5/2002 | Coulter et al. | |
| 6,403,106 B1 | 6/2002 | Sebag et al. | |
| 6,428,773 B1 | 8/2002 | Oko et al. | |
| 6,432,386 B1 | 8/2002 | Rollat-Corvol et al. | |
| 6,432,423 B1 | 8/2002 | Maignan et al. | |
| 6,491,927 B1 | 12/2002 | Arnaud et al. | |
| 6,503,761 B1 | 1/2003 | Koenig et al. | |
| 6,517,818 B1 | 2/2003 | Golz-Berner et al. | |
| 6,545,809 B1 * | 4/2003 | Phillips | 359/577 |
| 6,589,331 B2 | 7/2003 | Ostertag et al. | |
| 6,669,389 B2 | 12/2003 | Gueret | |
| 6,753,002 B2 | 6/2004 | George et al. | |
| 6,846,474 B2 | 1/2005 | Nayfeh et al. | |
| 7,056,498 B2 | 6/2006 | Chevalier et al. | |
| 7,060,371 B2 | 6/2006 | Akiyama et al. | |
| 7,168,874 B2 | 1/2007 | Gueret | |
| 7,258,900 B2 | 8/2007 | Raksha et al. | |
| 7,270,770 B2 | 9/2007 | Sage et al. | |
| 7,329,287 B2 | 2/2008 | Simonet et al. | |
| 7,329,719 B2 | 2/2008 | Pavlin | |
| 2001/0022025 A1 | 9/2001 | Skipper | |
| 2001/0033766 A1 | 10/2001 | Gueret | |
| 2002/0012683 A1 | 1/2002 | Henrion et al. | |
| 2002/0015965 A1 | 2/2002 | Sweeting | |
| 2002/0031870 A1 | 3/2002 | Bryant | |
| 2002/0039562 A1 | 4/2002 | Kobayashi et al. | |
| 2002/0041853 A1 | 4/2002 | Ishii et al. | |
| 2002/0064509 A1 | 5/2002 | Grimm et al. | |
| 2002/0070121 A1 | 6/2002 | Nayfeh et al. | |
| 2002/0117084 A1 | 8/2002 | Hayashi et al. | |
| 2002/0134282 A1 | 9/2002 | Ostertag et al. | |
| 2002/0169244 A1 | 11/2002 | Ostertag et al. | |
| 2002/0182383 A1 | 12/2002 | Phillips et al. | |
| 2002/0182409 A1 | 12/2002 | Gueret | |
| 2003/0007942 A1 | 1/2003 | Koenig | |
| 2003/0012752 A1 | 1/2003 | Bara | |
| 2003/0017124 A1 | 1/2003 | Agostini et al. | |
| 2003/0031870 A1 | 2/2003 | Argoitia et al. | |
| 2003/0039621 A1 | 2/2003 | Arnaud et al. | |
| 2003/0064039 A1 | 4/2003 | Kolodziej et al. | |
| 2003/0072602 A1 | 4/2003 | Gueret | |
| 2003/0134761 A1 | 7/2003 | Sebillotte-Arnaud et al. | |
| 2003/0180232 A1 | 9/2003 | Ishii et al. | |
| 2003/0180535 A1 | 9/2003 | Horino et al. | |
| 2004/0001869 A1 | 1/2004 | Yago et al. | |
| 2004/0009309 A1 | 1/2004 | Raksha et al. | |
| 2004/0012683 A1 | 1/2004 | Yamasaki et al. | |
| 2004/0105827 A1 | 6/2004 | Grimm et al. | |
| 2004/0109837 A1 | 6/2004 | Mellul et al. | |
| 2004/0175338 A1 | 9/2004 | Filippi et al. | |
| 2004/0228818 A1 | 11/2004 | Simon et al. | |
| 2004/0228890 A1 | 11/2004 | Blin et al. | |
| 2004/0241118 A1 | 12/2004 | Simon et al. | |
| 2005/0025728 A1 | 2/2005 | De Rigal et al. | |
| 2005/0036964 A1 | 2/2005 | Camus et al. | |
| 2005/0118122 A1 | 6/2005 | Simon et al. | |
| 2005/0191337 A1 | 9/2005 | Gueret | |
| 2005/0276767 A1 | 12/2005 | Blin et al. | |
| 2006/0018854 A1 | 1/2006 | Dumousseaux et al. | |
| 2006/0039876 A1 | 2/2006 | Dumousseaux et al. | |
| 2006/0041054 A1 | 2/2006 | Dumousseaux et al. | |
| 2006/0051382 A1 | 3/2006 | Vidal | |
| 2006/0088484 A1 | 4/2006 | Thevenet | |
| 2006/0099160 A1 | 5/2006 | Dumousseaux | |
| 2006/0165621 A1 | 7/2006 | Dubertret et al. | |
| 2006/0280764 A1 | 12/2006 | Watanabe et al. | |
| 2007/0009454 A1 | 1/2007 | Thevenet | |
| 2007/0231940 A1 | 10/2007 | Gourlaouen et al. | |
| 2008/0014158 A1 | 1/2008 | Lion et al. | |
| 2008/0044443 A1 | 2/2008 | Thevenet | |
| 2008/0050324 A1 | 2/2008 | Thevenet | |
| 2008/0105272 A1 | 5/2008 | Thevenet | |
| 2008/0124288 A1 | 5/2008 | Thevenet | |
| 2008/0127990 A1 | 6/2008 | Thevenet | |
| 2009/0130037 A1 | 5/2009 | Thevenet et al. | |

FOREIGN PATENT DOCUMENTS

| | | |
|---|---|---|
| DE | 102 19 296 | 11/2003 |
| EP | 0 080 976 | 6/1983 |
| EP | 0 096 459 | 12/1983 |
| EP | 0 113 920 | 7/1984 |
| EP | 0 388 582 | 9/1990 |
| EP | 0 412 704 | 2/1991 |
| EP | 0 412 707 | 2/1991 |
| EP | 0 416 747 | 3/1991 |
| EP | 0 581 651 | 2/1994 |
| EP | 0 582 152 | 2/1994 |
| EP | 0 587 908 | 3/1994 |
| EP | 0 686 858 | 12/1995 |
| EP | 0 749 747 | 12/1996 |
| EP | 0 815 836 | 1/1998 |
| EP | 0921217 | 12/1998 |
| EP | 0 955 039 | 10/1999 |
| EP | 0 962 224 | 12/1999 |
| EP | 1 043 018 | 10/2000 |
| EP | 1 101 486 | 5/2001 |
| EP | 1 184 426 | 3/2002 |
| EP | 1 217 046 | 6/2002 |
| EP | 1 264 562 | 12/2002 |
| EP | 1 318 184 | 6/2003 |
| EP | 1 382 323 | 1/2004 |
| EP | 1 410 786 | 4/2004 |
| EP | 1 411 069 | 4/2004 |
| EP | 1 424 372 | 6/2004 |
| EP | 1 440 681 | 7/2004 |
| FR | 2 077 143 | 10/1971 |
| FR | 2 232 303 | 1/1975 |
| FR | 2 268 512 | 11/1975 |
| FR | 2 393 573 | 1/1979 |
| FR | 2 594 130 | 8/1987 |
| FR | 2 845 277 | 4/2004 |
| FR | 2 845 899 | 4/2004 |
| FR | 2 847 812 | 6/2004 |
| FR | 2 848 821 | 6/2004 |
| FR | 2 848 826 | 6/2004 |
| FR | 2 850 271 | 7/2004 |
| FR | 2 851 463 | 8/2004 |
| GB | 1 331 819 | 9/1973 |
| GB | 1 510 674 | 5/1978 |
| GB | 2 355 987 | 5/2001 |
| JP | 51-137733 | 11/1976 |
| JP | 55-081809 | 6/1980 |
| JP | 58-206610 | 12/1983 |
| JP | 61-112008 | 5/1986 |
| JP | 63-175670 | 7/1988 |
| JP | 1-294611 | 11/1989 |
| JP | 2-111340 | 4/1990 |
| JP | 04-108710 | 8/1990 |
| JP | 3-284613 | 12/1991 |
| JP | 3-286463 | 12/1991 |
| JP | 4-292664 | 10/1992 |
| JP | 5-17710 | 1/1993 |
| JP | 7-258460 | 10/1995 |
| JP | 3-286463 | 11/1995 |
| JP | 7-304633 | 11/1995 |
| JP | 7-304997 | 11/1995 |
| JP | 7-316015 | 12/1995 |
| JP | 8-127513 | 5/1996 |
| JP | 9-188830 | 7/1997 |

| | | |
|---|---|---|
| JP | 10-158450 | 6/1998 |
| JP | 10-158541 | 6/1998 |
| JP | 2000-143490 | 11/1998 |
| JP | 11-012493 | 1/1999 |
| JP | 11-113631 | 4/1999 |
| JP | 11-181329 | 7/1999 |
| JP | 2001-61550 | 3/2001 |
| JP | 2001-299443 | 10/2001 |
| JP | 2002-188021 | 7/2002 |
| JP | 2002-194349 | 7/2002 |
| JP | 2002-322020 | 11/2002 |
| JP | 2003-000338 | 1/2003 |
| JP | 2003-024133 | 1/2003 |
| JP | 2003-199620 | 7/2003 |
| JP | 2004-043367 | 2/2004 |
| JP | 2004-043656 | 2/2004 |
| JP | 2004-059746 | 2/2004 |
| JP | 2004-123681 | 4/2004 |
| JP | 2004-131484 | 4/2004 |
| JP | 2004-307424 | 11/2004 |
| JP | 2005-232152 | 9/2005 |
| WO | WO 93/23009 | 11/1993 |
| WO | WO 93/23446 | 11/1993 |
| WO | WO 94/26729 | 11/1994 |
| WO | WO 95/00578 | 1/1995 |
| WO | WO 95/03776 | 2/1995 |
| WO | WO 95/06078 | 3/1995 |
| WO | WO 96/19347 | 6/1996 |
| WO | WO 97/35541 | 10/1997 |
| WO | WO 99/32076 | 7/1999 |
| WO | WO 99/36477 | 7/1999 |
| WO | WO 99/36478 | 7/1999 |
| WO | WO 01/38222 | 5/2001 |
| WO | WO 02/28356 | 4/2002 |
| WO | WO 03/016429 | 2/2003 |
| WO | WO 03/020225 | 3/2003 |
| WO | WO 04/000244 | 12/2003 |
| WO | WO 2004/007096 | 1/2004 |
| WO | WO 2004/009044 | 1/2004 |
| WO | WO 2006/027494 | 3/2006 |
| WO | WO 2006/037900 | 4/2006 |
| WO | WO 2006/037902 | 4/2006 |

OTHER PUBLICATIONS

Office Action mailed Jan. 8, 2009, in co-pending U.S. Appl. No. 11/242,901.
Office Action mailed Jun. 23, 2008, in co-pending U.S. Appl. No. 11/101,399.
Office Action mailed Jun. 23, 2008, in co-pending U.S. Appl. No. 11/242,901.
Office Action mailed Jun. 24, 2008, in co-pending U.S. Appl. No. 11/100,566.
Office Action mailed Jun. 24, 2008, in co-pending U.S. Appl. No. 11/770,177.
Office Action mailed Jun. 26, 2008, in co-pending U.S. Appl. No. 11/101,398.
Office Action mailed Mar. 20, 2008, in co-pending U.S. Appl. No. 11/101,400.
Titanium Dioxide—Wikipedia (http://en.wikipedia.org/wiki/Titanium_dioxide.retrieved online on Jun. 19, 2008).
Argoitia, A. et al., "Pigments Exhibiting Diffractive Effects", Society of Vacuum Coaters, 45th Annual Technical Conference Proceedings, pp. 539-545, (2002).
Co-pending U.S. Appl. No. 10/529,872, filed Apr. 1, 2005.
Co-pending U.S. Appl. No. 11/100,509, filed Apr. 7, 2005.
Co-pending U.S. Appl. No. 11/100,514, filed Apr. 7, 2005.
Co-pending U.S. Appl. No. 11/100,566, filed Apr. 7, 2005.
Co-pending U.S. Appl. No. 11/101,398, filed Apr. 8, 2005.
Co-pending U.S. Appl. No. 11/101,399, filed Apr. 8, 2005.
Co-pending U.S. Appl. No. 11/101,400, filed Apr. 8, 2005.
Co-pending U.S. Appl. No. 11/242,900, filed Oct. 5, 2005.
Co-pending U.S. Appl. No. 11/242,901, filed Oct. 5, 2005.
English language Abstract of DE 102 19 296, Nov. 20, 2003.
English language Patent Abstract of Japan of JP 04-108710, Aug. 27, 1990.
English language Patent Abstract of Japan of JP 10-158541, Jun. 16, 1998.
English language Patent Abstract of Japan of JP 10-158450, Jun. 16, 1998.
English Language Patent Abstracts of Japan of JP 11-012493, Jan. 19, 1999.
English language Patent Abstract of Japan of JP 1-294611, Nov. 28, 1989.
English language Patent Abstract of Japan of JP 2000-143490, Nov. 9, 1998.
English language Patent Abstract of Japan of JP 2003-199620, Jul. 15, 2003.
English language Patent Abstract of Japan of JP 2-111340, Apr. 24, 1990.
English language Patent Abstract of Japan of JP 3-286463, Dec. 17, 1991.
English language Patent Abstract of Japan of JP 5-17710, Jan. 26, 1993.
English language Patent Abstract of Japan of JP 7-258460, Oct. 9, 1995.
English language Patent Abstract of Japan of JP 7-304633, Nov. 21, 1995.
English language Patent Abstract of Japan of JP 7-304997, Nov. 21, 1995.
English language Patent Abstract of Japan of JP 8-127513, May 21, 1996.
English language Patent Abstract of Japan of JP 9-188830, Jul. 22, 1997.
French Search Report for French Patent Application No. FR 04/50712, priority document for the present U.S. Appl. No. 11/100,513, Nov. 9, 2004.
French Search Report for French Patent Application No. FR 04/50713, priority document for co-pending U.S. Appl. No. 11/100,566, Nov. 23, 2004.
French Search Report for French Patent Application No. FR 04/50714, priority document for co-pending U.S. Appl. No. 11/100,509, Nov. 10, 2004.
French Search Report for French Patent Application No. FR 04/50715, priority document for co-pending U.S. Appl. No. 11/100,514, Nov. 23, 2004.
French Search Report for French Patent Application No. FR 05/52124, May 24, 2006.
Furst, E. et al., "Permanently Linked Monodisperse Paramagnetic Chains", Langmuir, vol. 14, pp. 7334-7336 (1998).
Goubault, C., "Flexible Magnetic Filaments as Micromechanical Sensors", Physical Review Letters, vol. 91, No. 26, pp. 1-4 (2003).
International Cosmetic Ingredient Dictionary and Handbook, 1997 Edition, pp. 371-386.
International Cosmetic Ingredient Dictionary and Handbook, 1997 Edition, pp. 524-528.
International Search Report for PCT Application No. PCT/IB03/04306, priority document for co-pending U.S. Appl. No. 10/529,872, dated Mar. 3, 2004.
International Search Report for PCT/FR2005/050557, priority document for co-pending U.S. Appl. No. 11/242,901, dated Feb. 10, 2006.
Office Action mailed Dec. 28, 2006 in co-pending U.S. Appl. No. 11/100,509.
English language Abstract of JP 4-292664, Oct. 16, 1992.
Co-pending U.S. Appl. No. 11/770,177, filed Jun. 28, 2007.
Office Action mailed Aug. 16, 2007, in co-pending U.S. Appl. No. 11/101,400.
Patent Abstract of Japan for JP 11-113631, Apr. 27, 1999.
Patent Abstract of Japan for JP 2001-61550, Mar. 13, 2001.
English language Abstract of FR 2268512, Dec. 26, 1976.
English language Abstract of FR 2594130, Aug. 14, 1987.
English language Abstract of JP 02-111340, Apr. 24, 1990.
English language Abstract of JP 03-286463, Dec. 12, 1991.
English language Abstract of JP 04-292664, Oct. 16, 1992.
English language Abstract of JP 05-017710, Jan. 26, 1993.
English language Abstract of JP 07-258460, Oct. 9, 1995.
English language Abstract of JP 07-316015, Dec. 5, 1995.
English language Abstract of JP 09-188830, Jul. 22, 1997.
English language Abstract of JP 10-158540, Jun. 16, 1998.

English language Abstract of JP 10-158541, Jun. 16, 1998.
English language Abstract of JP 11-113631, Apr. 27, 1999.
English language Abstract of FR 2776509, Oct. 1, 1999.
English language Abstract of EP 1043018, Oct. 11, 2000.
English language Abstract of FR 2845899, Oct. 18, 2002.
English language Abstract of EP 0955039, Mar. 11, 1999.
English language Abstract of JP 2001-061550, Mar. 13, 2001.
English language Abstract of EP 1410784, Apr. 24, 2001.
English language Abstract of EP 1101486, May 23, 2001.
English language Abstract of JP 2002-188021, Jul. 5, 2002.
English language Abstract of EP 1264562, Dec. 6, 2002.
English language Abstract of JP 2003-199620, Jul. 15, 2003.
English language Abstract of DE 10219296, Nov. 20, 2003.
English language Abstract of EP 1382323, Jan. 21, 2004.
English language Abstract of FR 2845277, Apr. 15, 2004.
English language Abstract of EP 1410786, Apr. 21, 2004.
English language Abstract of JP 2004-131484, Apr. 30, 2004.
English language Abstract of FR 2848826, Jun. 25, 2004.
English language Abstract of FR 2848821, Jun. 25, 2004.
English language Abstract of FR 2851463, Aug. 27, 2004.
Office Action mailed Mar. 19, 2009, in co-pending U.S. Appl. No. 11/101,398.
Office Action mailed Mar. 19, 2009, in co-pending U.S. Appl. No. 11/101,399.
Office Action mailed Jul. 9, 2009, in co-pending U.S. Appl. No. 11/100,566.
Office Action mailed Jul. 10, 2009, in co-pending U.S. Appl. No. 11/770,177.
"Graft Copolymers with Short Side Chains," Polymer Letters, 1967, vol. 5, pp. 477-481.
Fermigier, et al., "Suspensions de Particules Magnetiques," Bulletin de la S.F.P. (105): pp. 2-5, Jul. 1996.
Goubault, "Colloides Magnetiques: Auto-Organisation et Applications Biologiques," Doctoral Thesis of the University of Paris VI, Mar. 23, 2004.
Hansen, C.M., "The Three Dimensional Solubility Parameter—Key to Paint Component Affinities: I. Solvents, Plasticizers, Polymers, and Resins," Journal of Paint Technology, vol. 39, No. 505, pp. 104-117 (1967).
Office Action mailed Jan. 21, 2010, in co-pending U.S. Appl. No. 11/242,901.
Office Action mailed Jul. 7, 2009, in copending U.S. Appl. No. 11/242,901.
Office Action mailed Nov. 9, 2009, in co-pending U.S. Appl. No. 11/101,400.
Office Action mailed Oct. 1, 2009, in co-pending U.S. Appl. No. 11/101,398.
Office Action mailed Sep. 24, 2009, in co-pending U.S. Appl. No. 11/101,399.
Office Action mailed Apr. 27, 2010, in co-pending U.S. Appl. No. 11/770,177.
Office Action mailed Apr. 28, 2010, in co-pending U.S. Appl. No. 11/100,566.
Office Action mailed Aug. 3, 2010, in co-pending U.S. Appl. No. 11/101,399.
Office Action mailed Aug. 4, 2010, in co-pending U.S. Appl. No. 11/101,398.
Office Action mailed Jul. 7, 2010, in co-pending U.S. Appl. No. 11/242,901.
Office Action mailed May 11, 2010, in co-pending U.S. Appl. No. 11/101,400.
Drahl, "Nail Polish", 2008, American Chemical Society, Chemical & Engineering News, vol. 86, No. 32, p. 32.
English language Abstract of JP 51-137733, dated Nov. 27, 1976.
English language Abstract of JP 63-175670, dated Jul. 20, 1988.
Japanese Office Action in related Application No. 2007-534054, dated Oct. 7, 2010.
Office Action mailed Dec. 21, 2010, in co-pending U.S. Appl. No. 11/101,400.
Office Action mailed Dec. 22, 2010, in co-pending U.S. Appl. No. 11/242,901.
Office Action mailed Dec. 23, 2010, in co-pending U.S. Appl. No. 11/242,900.

* cited by examiner

COMPOSITION FOR APPLICATION TO THE SKIN, TO THE LIPS, TO THE NAILS, AND/OR TO HAIR

This non-provisional application claims the benefit of French Application No. 04/50712 filed on Apr. 8, 2004, and U.S. Provisional Application No. 60/564,971, filed on Apr. 26, 2004, both of which are hereby incorporated by reference.

The present disclosure relates to cosmetic compositions for application to the skin, including the mucous membranes such as the lips, to the nails, or to hair, such as the eyelashes, the eyebrows, and head hair.

The preparation of compositions including a coloring agent that can reflect light and/or modify the visual perception of the cosmetic composition is known. In association with such a coloring agent, it is known to incorporate into the composition pigments of an organic or inorganic nature in the pure form, which may have the disadvantage of reducing the transparency of the composition so that the maximum benefit of the optical effects produced by said coloring agent cannot be enjoyed.

There is a need for a cosmetic composition having satisfactory color and including a coloring agent that can produce a specific optical effect that is sufficiently visible.

One aspect of the present disclosure provides a composition for application to the skin, to the lips, to the nails, and/or to hair, the composition comprising:
- at least one first coloring agent in an amount sufficient to color the composition, comprising particles of at least one composite pigment, said particles comprising an inorganic core at least partially coated with at least one organic coloring substance; and
- at least one second coloring agent in an amount sufficient to produce a specific optical effect in the composition which is visibly perceptible to a human observer.

The specific optical effect may be a sparkle effect, a goniochromatic effect, a speckled effect, or any other desired optical effect.

A sparkle effect may, for example, result in highlight points in the composition, contrasting with the surrounding color. The highlight points may be due to reflective particles, for example.

A goniochromatic effect results in a variation in color as a function of the angle of observation.

A speckled effect may result in the composition having speckles of color present therein that are visible to the eye, the speckles being due, for example, to flakes or fibers.

In another aspect of the present disclosure, compositions can be obtained that are both colored and have an optical effect that is visible to the naked eye due to the presence of the second coloring agent.

For example, the first coloring agent present in the composition may provide color, while preserving the transparency or translucence desired in the composition so that the optical effect provided by the second coloring agent remains visible to the naked eye.

The at least one first coloring agent may be present in the composition in an amount ranging from 0.1% to 20% by weight relative to the total composition weight. In one embodiment, the at least one first coloring agent may be present in the composition in an amount ranging from 0.1% to 10% by weight relative to the total composition weight. In another embodiment, the at least one first coloring agent may be present in the composition in an amount ranging from 0.5% to 5% by weight relative to the total composition weight.

In exemplary embodiments, the amount of the first coloring agent may be less than the amount of the second coloring agent.

In one embodiment, the composite pigment is not an interference pigment.

The organic coloring substance may be different from melanin.

An interference pigment is for example a pigment comprising a superposition of layers of constant thickness of materials selected to produce optical interferences. An example of an interference pigment is disclosed in U.S. Pat. No. 6,428,773.

The saturation C* of the composite pigment may be above about 30, measured according to the following protocol.

Protocol for Measuring the Saturation C* of the Composite Pigment:

The color values a* and b* in the CIE L*a*b* colorspace of the composite pigment are measured as follows.

The composite pigment in a raw state is compacted in a rectangular cup having dimensions of 2×1.5 cm and a depth of 3 mm, by applying a pressure of 100 bars.

The a* and b* values of the compacted pigment are measured with a Minolta 3700d spectrophotometer, in mode specular excluded under illuminant D65 and medium aperture. The saturation is computed as $C^*=(a^{*2}+b^{*2})^{1/2}$.

The at least one second coloring agent may be present in the composition in an amount ranging from 0.1% to 50% by weight relative to the total composition weight. In one embodiment, the at least one second coloring agent may be present in the composition in an amount ranging from 0.5% to 40% by weight relative to the total composition weight. In another embodiment, the at least one second coloring agent may be present in the composition in an amount ranging from 1% to 20% by weight relative to the total composition weight.

The weight ratio of the at least one second coloring agent to the at least one first coloring agent may range from 0.1 to 50. In one embodiment, the weight ratio of the at least one second coloring agent to the at least one first coloring agent may range from 0.5 to 30. In another embodiment, the weight ratio of the at least one second coloring agent to the at least one first coloring agent may range from 1 to 10.

A suitable tint may be obtained in a variety of manners, such as, for example, by mixing the composite pigments of the present disclosure, wherein the pigments have different colors, and/or by the presence of a plurality of organic coloring substances in the coating of the cores of the composite pigment or pigments, the organic coloring substances being mixed or present within the respective layers of the coating.

The term "at least partially coated" as used in the present disclosure means coating all or a portion of the inorganic core.

The composition of the present disclosure may include a physiologically acceptable medium.

The term "physiologically acceptable medium" means a non-toxic medium that can be applied to the skin, the lips, the nails, or hair of human beings, and may comprise a cosmetic medium. The physiologically acceptable medium will be adapted to the nature of the surface onto which the composition is to be applied, and to the form in which the composition is intended to be packaged, such as a solid or a fluid at ambient temperature and atmospheric pressure.

The term "cosmetic composition" means a composition as defined in Council Directive 93/35/EEC dated 14 Jun. 1993.

Composite Pigment of First Coloring Agent

Structure

A composite pigment of the at least one first coloring agent of the present disclosure may be composed of particles comprising an inorganic core at least partially coated with at least one organic coloring substance.

At least one binder may contribute to fixing the at least one organic coloring substance onto the inorganic core.

The particles of a composite pigment may have a variety of forms. In one embodiment, the particles may be in the form of flakes or they may be globular, such as spherical, and may be hollow or solid. The term "in the form of flakes" means particles for which the ratio of the largest dimension to the thickness is 5 or more.

A composite pigment of the present disclosure can, for example, have a specific surface area ranging from 1 m$^2$/g (square meters/gram) to 1000 m$^2$/g. In one embodiment, the composite pigment can have a specific surface area ranging from 10 m$^2$/g to 600 m$^2$/g. In another embodiment, the composite pigment can have a specific surface area ranging from 20 m$^2$/g to 400 m$^2$/g. The specific surface area is the value measured using the BET (Brunauer-Emmett-Teller) method.

The amount of the core in the composite pigment may exceed 50% by weight relative to the total weight of the composite pigment. In one embodiment, the core may be present in the composite pigment in an amount ranging from 50% to 70% by weight relative to the total weight of the composite pigment. In another embodiment, the core may be present in the composite pigment in an amount ranging from 60 to 70%.

A composition may include one or more composite pigments solely of the kind defined above or, in a variation, it may include one or more other composite pigments as well as pigments having a non-composite structure such as mineral pigments, lakes, or organic pigments. The composition can also be free of uncoated TiO$_2$ particles.

The composite pigment of the present disclosure may be different from the at least one second coloring agent, which is adapted to produce a specific optical effect in the composition. The composite pigment can thus be a pigment other than an interference pigment.

Inorganic Core

The inorganic core may have any form that is suitable for fixing particles of organic coloring substance. Among inorganic core forms that may be used, non-limiting mention may be made of spherical, globular, granular, polyhedral, acicular, spindle-shaped, flattened flake, rice grain, and scale forms, as well as combinations of these forms.

In one embodiment of the present disclosure, the ratio of the largest dimension of the inorganic core to its smallest dimension ranges from 1 to 50.

The inorganic core may have a mean size ranging from 1 nm (nanometer) to about 100 nm. In one embodiment, the inorganic core may have a mean size ranging from 5 nm to 75 nm. In yet another embodiment, the inorganic core may have a mean size ranging from 10 nm to 50 nm.

The term "mean size" means the dimension given by the statistical grain size distribution curve at 50% population, termed D50. The mean size may be a number average determined by image analysis such as electron microscopy.

The inorganic core may have a refractive index not less than 2. In one embodiment the inorganic core may have a refractive index not less than 2.1. In a further embodiment, the inorganic core may have a refractive index not less than 2.2.

Among the materials that may be used to form the inorganic core, non-limiting mention may be made of metallic salts, metal oxides such as oxides of titanium, zirconium, cerium, zinc, iron, iron blue, aluminum, and chromium, aluminas, glasses, ceramics, graphite, silicas, silicates such as aluminosilicates and borosilicates, synthetic micas, and mixtures thereof.

In one embodiment, the inorganic core is chosen from oxides of titanium, such as TiO$_2$, iron, such as Fe$_2$O$_3$, cerium, zinc, and aluminum, silicas and silicates, such as aluminosilicates and borosilicates.

The inorganic core may have a specific surface area, measured using the BET method, ranging from 1 m$^2$/g to 1000 m$^2$/g. In one embodiment, the inoarganic core may have a specific surface area ranging from 10 m$^2$/g to 600 m$^2$/g. In another embodiment, the inorganic core may have a specific surface area ranging from 20 m$^2$/g to 400 m$^2$/g.

The inorganic core may be colored.

Organic Coloring Substance

The at least one organic coloring substance may, for example, comprise at least one organic pigment such as at least one organic lake or other organic pigment.

The at least one organic coloring substance may, for example, be chosen from particular compounds that are insoluble in the physiologically acceptable medium of the composition.

The at least one organic coloring substance may, for example, comprise pigments, such as organic lakes or other pigments, which may be chosen from the following compounds and the mixtures thereof:

cochineal carmine;

organic pigments of azo, anthraquinone, indigo, xanthene, pyrene, quinoline, triphenylmethane, and fluorane dyes;

organic lakes or organic insoluble salts of sodium, potassium, calcium, barium, aluminum, zirconium, strontium, titanium, or of acid dyes such as azo, anthraquinone, indigo, xanthene, pyrene, quinoline, triphenylmethane, or fluorine dyes, which dyes may comprise at least one carboxylic or sulfonic acid group.

Among organic pigments that may be used, not-limiting mention may be made of D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, and FD&C Yellow No. 6.

In one embodiment, the at least one organic coloring substance may comprise an organic lake supported by an organic support such as colophane or aluminum benzoate, for example.

Among organic lakes that may be used, non-limiting mention may be made of D&C Red No. 2 Aluminum lake, D&C Red No. 3 Aluminum lake, D&C Red No. 4 Aluminum lake, D&C Red No. 6 Aluminum lake, D&C Red No. 6 Barium lake, D&C Red No. 6 Barium/Strontium lake, D&C Red No. 6 Strontium lake, D&C Red No. 6 Potassium lake, D&C Red No. 7 Aluminum lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminum lake, D&C Red No. 9 Barium lake, D&C Red No. 9 Barium/Strontium lake, D&C Red No. 9 Zirconium lake, D&C Red No. 10 Sodium lake, D&C Red No. 19 Aluminum lake, D&C Red No. 19 Barium lake, D&C Red No. 19 Zirconium lake, D&C Red No. 21 Aluminum lake, D&C Red No. 21 Zirconium lake, D&C Red No. 22 Aluminum lake, D&C Red No. 27 Aluminum lake, D&C Red No. 27 Aluminum/Titanium/Zirconium lake, D&C Red No. 27 Barium lake, D&C Red No. 27 Calcium lake, D&C Red No. 27 Zirconium lake, D&C Red No. 28 Aluminum lake, D&C Red No. 30 lake, D&C Red No. 31 Calcium lake, D&C Red No. 33 Aluminum lake, D&C Red No. 34 Calcium lake, D&C Red No. 36 lake, D&C Red No. 40 Aluminum lake, D&C Blue No. 1 Aluminum lake, D&C Green No. 3 Aluminum lake, D&C Orange No. 4 Aluminum lake, D&C Orange No. 5 Aluminum lake, D&C Orange No. 5 Zirconium lake, D&C Orange No. 10 Aluminum lake, D&C Orange No. 17 Barium lake, D&C Yellow No. 5 Aluminum lake, D&C Yellow No. 5 Zirconium lake, D&C Yellow No. 6 Aluminum lake, D&C Yellow No. 7 Zirconium lake, D&C Yellow No. 10 Aluminum lake, FD&C Blue No. 1 Aluminum lake, FD&C Red No. 4 Aluminum lake, FD&C Red No. 40 Aluminum lake, FD&C Yellow No. 5 Aluminum lake, and FD&C Yellow No. 6 Aluminum lake.

The chemical compounds corresponding to each of the organic coloring substances listed above are mentioned in the work entitled "International Cosmetic Ingredient Dictionary and Handbook", 1997 edition, pages 371 to 386 and 524 to 528, published by "The Cosmetic, Toiletry, and Fragrance Association", the contents of which are hereby incorporated by reference.

The proportion by weight of the at least one organic coloring substance may range from 10 parts to 500 parts by weight per 100 parts of inorganic core. In one embodiment, the proportion by weight of the at least one organic coloring substance may range from 20 parts to 250 parts by weight per 100 parts of inorganic core. In another embodiment of the present disclosure, the proportion by weight of the at least one organic coloring substance may range from 40 parts to 125 parts by weight per 100 parts of inorganic core.

The amount of the organic coloring substance in the composite pigment may exceed 30% by weight relative to the total weight of the composite pigment. In one embodiment of the present disclosure, the organic coloring substance may be present in the composite pigment in an amount ranging from 30% to 50% by weight relative to the total weight of the composite pigment. In another embodiment of the present disclosure, the organic coloring substance may be present in an amount ranging from 30% to 40% by weight relative to the total weight of the composite pigment.

Binder

The at least one binder may be of any type provided that it allows the at least one organic coloring substance to adhere to the surface of the inorganic core.

The at least one binder may be organic.

Among binders that may be used, non-limiting mention may be made of silicone compounds, polymeric compounds, oligomeric compounds, such as organosilanes, fluoroalkylated organosilanes and polysiloxanes, including polymethylhydrogen siloxane, as well as to variety of coupling agents such as coupling agents based on silanes, titanates, aluminates, zirconates, and mixtures thereof.

Among silicone compounds that may be used, non-limiting mention may be made of:
  organosilanes (1) obtained from alkoxysilanes;
  polysiloxanes (2) which may optionally be modified, chosen from the following non-limiting list:
    modified polysiloxanes (2A) comprising at least one radical chosen from, for example, polyethers, polyesters and epoxy compounds (termed "modified polysiloxanes" below);
    polysiloxanes (2B) carrying, on one silicon atom located at the end of the polymer, at least one group chosen from the following non-limiting list: carboxylic acids, alcohols, and hydroxyl groups; and
  fluoroalkylated organosilane compounds (3) obtained from fluoroalkylsilanes.

The organosilane compounds (1) may be obtained from alkoxysilane compounds represented by formula (I):

wherein:
  $R^1$ is chosen from $C_6H_5-$, $(CH_3)_2CH-CH_2-$ and $C_bH_{2b+1}$-type radical (in which b ranges from 1 to 18);
  X is chosen from $CH_3O-$ and $C_2H_5O-$; and
  a ranges from 0 to 3.

Specific examples of alkoxysilane compounds may include alkoxysilanes chosen from: methyltriethoxysilane, dimethyldiethoxysilane, phenyltriethoxysilane, diphenyldiethoxysilane, methyltrimethoxysilane, dimethyldimethoxysilane, phenyltrimethoxysilane, diphenyldimethoxysilane, isobutyltrimethoxysilane, decyltrimethoxysilane, and the like. In one embodiment of the present disclosure, the alkoxysilane compounds are chosen from methyltriethoxysilane, phenyltriethoxysilane, methyltrimethoxysilane, dimethyldimethoxysilane, and isobutyltrimethoxysilane. In yet another embodiment, the alkoxysilane compounds are chosen from methyltriethoxysilane, methyltrimethoxysilane, and phenyltriethoxysilane.

The polysiloxanes (2) may be chosen from polysiloxanes of formula (II):

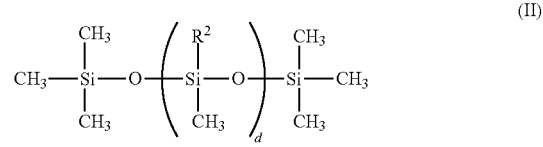

wherein $R^2$ is chosen from H— and $CH_3$— and d ranges from 15 to 450.

In one embodiment, $R^2$ is H.

In an embodiment of the present disclosure, the modified polysiloxanes (2A) may be chosen from:
  ($a^1$) modified polysiloxanes carrying polyethers, represented by formula (III):

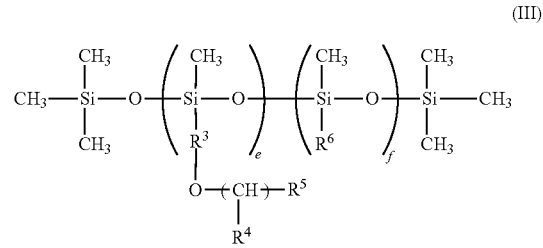

wherein:
  $R^3$ comprises $-(CH_2)_h-$;
  $R^4$ comprises $-(CH_2)_i-CH_3$;
  $R^5$ is chosen from $-OH$, $-COOH$, $-CH=CH_2$, $-C(CH_3)=CH_2$ and $-(CH_2)_j-CH_3$;
  $R^6$ comprises $-(CH_2)_k-CH_3$;
  g and h independently range from 1 to 15;
  j and k independently range from 0 to 15;
  e ranges from 1 to 50; and
  f ranges from 1 to 300;
  ($a^2$) modified polysiloxanes carrying polyesters, represented by formula (IV):

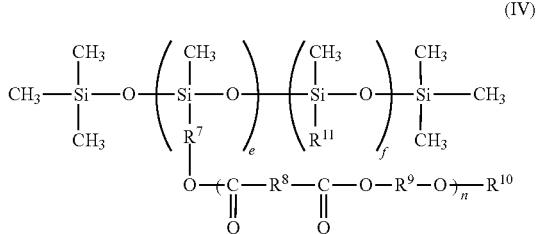

(IV)

wherein:
$R^7$, $R^8$ and $R^9$ independently comprise $-(CH_2)_q-$;
$R^{10}$ is chosen from $-OH$, $-COOH$, $-CH=CH_2$, $-C(CH_3)=CH_2$ and $-(CH_2)_n-CH_3$;
$R^{11}$ comprises $-(CH_2)_s-CH_3$;
n and q independently range from 1 to 15,
r and s independently range from 0 to 15;
e ranges from 1 to 50; and
f ranges from 1 to 300;
  (a³) modified polysiloxanes carrying epoxy radicals represented by formula (V):

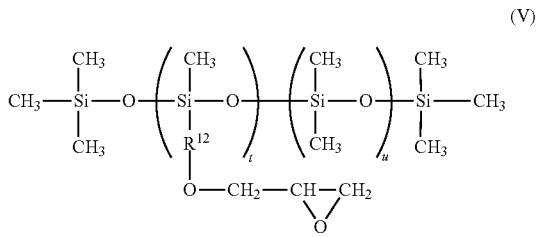

(V)

wherein:
$R^{12}$ comprises $-(CH_2)_v-$;
v ranges from 1 to 15;
t ranges from 1 to 50; and
u ranges from 1 to 300; and
  mixtures of modified polysiloxanes represented by formulas (III), (IV), and (V).

In one embodiment, modified polysiloxanes (2A) are modified polysiloxanes carrying polyethers with formula (III).

Polysiloxanes modified at the terminal portion (2B) may have formula (VI):

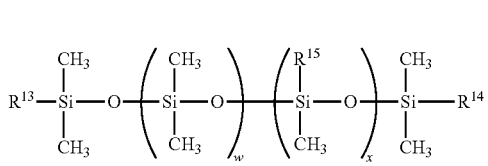

(VI)

wherein:
$R^{13}$ and $R^{14}$ are independently chosen from $-OH$, $R^{16}-OH$, and $R^{17}-COOH$;
$R^{15}$ is chosen from $-CH_3$ and $-C_6H_5$;
$R^{16}$ and $R^{17}$ comprise $-(CH_2)_y-$;
y ranges from 1 to 15;
w ranges from 1 to 200; and
x ranges from 0 to 100.

In one embodiment of the present disclosure, polysiloxanes modified on at least one end include those carrying at least one radical ($R^{16}$ and/or $R^{17}$) carrying a carboxylic acid group on at least one terminal silicon atom.

Fluoroalkylated organosilane compounds (3) may be obtained from fluoroalkylsilanes represented by formula (VII):

$$CF_3(CF_2)_zCH_2CH_2(R^{18})_aSiX_{4-a} \quad (VII)$$

wherein:
$R^{18}$ is chosen from $CH_3-$, $C_2H_5-$, $CH_3O-$, and $C_2H_5O-$;
X is chosen from $CH_3O-$ and $C_2H_5O-$;
z ranges from 0 to 15; and
a ranges from 0 to 3.

In an embodiment of the present disclosure, the fluoroalkylsilanes may be chosen from the following non-limiting list: trifluoropropyltrimethoxysilane, tridecafluorooctyltrimethoxysilane, heptadecafluorodecyltrimethoxysilane, heptadecafluorodecylmethyldimethoxysilane, trifluoropropyltriethoxysilane, tridecafluorooctyltriethoxysilane, heptadecafluorodecyltriethoxysilane, heptadecafluorodecylmethyldiethoxysilane and the like. In a further embodiment of the present disclosure, the fluoroalkylsilanes may be chosen from trifluoropropyltrimethoxysilane, tridecafluorooctyltrimethoxysilane and heptadecafluorodecyltrimethoxysilane. In yet another embodiment of the present disclosure, the fluoroalkylsilanes may be chosen from trifluoropropyl trimethoxysilane and tridecafluorooctyltrimethoxysilane.

Among silane-based coupling agents that may be used, non-limiting mention may be made of vinyltrimethoxysilane, vinyltriethoxysilane, γ-aminopropyl-triethoxysilane, γ-glycidoxypropyltrimethoxysilane, γ-mercaptopropyltrimethoxysilane, 7-methacryloxypropyltrimethoxysilane, N-β(aminoethyl)-γ-aminopropyltrimethoxysilane, γ-glycidoxypropylmethyldimethoxysilane, γ-chloropropyltrimethoxysilane, and the like.

Among titanate-based coupling agents that may be used, non-limiting mention may be made of isopropylstearoyl titanate, isopropyltris(dioctylpyrophosphate) titanate, isopropyltri(N-aminoethyl-aminoethyl) titanate, tetraoctylbis (ditridecylphosphate) titanate, tetra(2,2-diaryloxymethyl-1-butyl)bis(ditridecyl)phosphate titanate, bis(dioctylpyrophosphate)oxyacetate titanate, bis(dioctylpyrophosphate)ethylene titanate, and the like.

The aluminate-based coupling agents may be chosen from acetoalkoxyaluminum diisopropylate, aluminum diisopropoxymonoethylacetoacetate, aluminum trisethylacetoacetate, aluminum trisacetylacetonate, and the like.

The zirconate-based coupling agents may be chosen from zirconium tetrakisacetylacetonate, zirconium dibutoxybisacetylacetonate, zirconium tetrakisethylacetoacetate, zirconium tributoxymonoethylacetoacetate, zirconium tributoxyacetylacetonate, and the like.

The binders may have a molar mass in the range 300 to 100 000.

In one embodiment of the present disclosure, the at least one binder is in a liquid state or is soluble in water or other solvents to obtain a layer which uniformly coats the inorganic cores.

The at least binder may be present in an amount ranging from 0.01% to 15% by weight (calculated with respect to C or Si) relative to the weight of particles comprising the core and the binder. In one embodiment, the at least binder may be present in an amount ranging from 0.02% to 12.5% by weight (calculated with respect to C or Si) relative to the weight of particles comprising the core and the binder. In another embodiment, the at least binder may be present in an amount ranging from 0.03% to 10% by weight (calculated with respect to C or Si) relative to the weight of particles comprising the core and the binder. Further details regarding the calculation of the relative quantity of binder can be found in European Patent Application No. EP 1 184 426 A2. The at least one binder may be present in an amount less than 5% or even less than 3% by weight relative to the total weight of the composite pigment.

Preparation of Composite Pigment

The composite pigment may be manufactured by any appropriate method, for example a mechano-chemical method or a method of precipitation in solution, with dissolution of an organic coloring substance and a precipitation thereof at the surface of the core.

A binder may or may not be used.

In one embodiment, the composite pigment may be manufactured by a method comprising a mechanical mixing of an organic pigment and the inorganic core. A binder may be added and mixed with the inorganic core before the introduction of the organic coloring substance.

The composite pigment may, for example, be produced using one of the processes described in European Patent Application Nos. EP 1 184 426 and EP 1 217 046, the contents of which are hereby incorporated by reference. In one embodiment, the composite pigments are produced by the process described in European Patent Application No. EP 1 184 426.

In an embodiment of the present disclosure, the particles comprising the inorganic core are first mixed with the at least one binder.

So that the binder can adhere uniformly to the surface of the inorganic core, the particles may be passed initially through a mill to disaggregate them.

The mixing and agitation conditions are selected so that the core can be uniformly coated with binder. The conditions may be controlled so that the linear load ranges from 19.6 N/cm (newtons/centimeter) to 19160 N/cm. In one embodiment, the linear load ranges from 98 N/cm to 14170 N/cm. In a further embodiment, the linear load ranges from 147 N/cm to 980 N/cm. The treatment time ranges from 5 minutes to 24 hours, and in one embodiment, ranges from 10 minutes to 20 hours. The rotation rate may range from 2 rpm (revolutions per minute) to 1000 rpm. In one embodiment, the rotation rate ranges from 5 rpm to 1000 rpm, and in a further embodiment, the rotation rate ranges from 10 rpm to 800 rpm.

After coating the inorganic core with the at least one binder, the at least one organic coloring substance is added and mixed with agitation so that it adheres to the layer of binder.

Examples of addition methods are continuous addition in large quantities, or in small quantities.

Mixing and agitation, whether of the inorganic cores with the at least one binder or of the at least one organic coloring substance with the inorganic cores coated with binder, may be carried out using an apparatus which can apply a sharp shearing and/or compressive force to the mixture of powders. Examples of apparatus of that type are roller mixers, blade mixers, and the like. In one embodiment, roller mixers are used. A list of suitable apparatus is given in European Patent Application No. EP 1 184 426 A2.

A further method for manufacturing a composite pigment has been described in Japanese Patent JP 3286463, which discloses a solution precipitation process.

The at least one organic coloring substance is dissolved in ethanol and the inorganic cores are then dispersed in said ethanolic solution.

An aqueous alkaline solution of sodium or potassium carbonate is then slowly added to these mixtures, and finally, an ethanolic calcium chloride solution is slowly added, with constant agitation.

Second Coloring Agent

The at least one second coloring agent can produce a specific optical effect in the composition.

The at least one second coloring agent can comprise, for example, reflective particles, pearlescent agents (or "nacres"), and/or a goniochromatic coloring agents.

The at least one second coloring agent may comprise particles having the form of flakes or it may be in a globular form.

The at least one second coloring agent may have a multi-layered structure.

Among substrates that may be use when the at least one second coloring agent has a multilayered structure, non-limiting mention may be made of substrates comprising at least one material chosen from metals, metal oxides, and polymers.

The at least one second coloring agent may comprise at least one material chosen from micas, synthetic micas, talc, silicas, and aluminas.

The at least one second coloring agent may comprise particles based on glass, surface-metallized particles, or particles comprising a metal chosen from aluminum, bronze, copper, and alloys thereof.

Reflective Particles

The term "reflective particles" as used in the context of the present disclosure means particles the size and structure of which, in particular the thickness of the layer or layers constituting them and their physical and chemical natures, and their surface state, allow them to reflect incident light. In one embodiment, the reflection may have sufficient intensity to create highlight points on the surface of the composition of the present disclosure, when the composition is applied to the surface to be made up, which highlight points are visible to the naked eye, i.e. they are points of greater brightness that contrast with their environment and appear to shine.

In one embodiment, the reflective particles may occlude the visual perception of the curvature of the made-up surface by preventing the eye of the observer from obtaining a lock, the highlight points being capable of appearing or disappearing in a random manner when the made-up surface and the observer are moving.

The reflective particles may also be selected in a manner such that they do not significantly alter the coloring effect generated by the first coloring agent associated therewith, or even to optimize that effect in terms of color yield. In one embodiment, the reflective particles may have a yellow, pink, red, bronze, orangey, brown, and/or copper glint.

The reflective particles used should be compatible with cosmetic use and they should be able to subsist in a physiologically acceptable medium; in particular, they should not be dissolved therein, or in any case they should not dissolve entirely therein.

The solid particles may be in various forms. In one embodiment, the particles may be in the form of flakes, or they may be globular, such as spherical.

Particles with a substantially planar outer surface are also suitable since, if their size, structure, and surface state allow it, they readily give rise to an intense specular reflection. This is known as a mirror effect.

For such particles, it is essentially the light returned by reflection in one direction making the same angle with the normal to the reflective surface as the angle made by the incident light to that normal, which allows the particles to appear as highlight points, and not the light diffused in all other directions.

In one embodiment, the reflective particles may be non-diffusing and non-matt.

In another embodiment, the reflective particles do not substantially alter the color of the cosmetic composition.

In an embodiment where the reflective particles do not substantially alter the color of the cosmetic composition, reflective particles which allow a metallic reflection of incident light may be used. Such metallic reflection can occur when the reflective particles, whatever their shape, can allow reflection onto a layer of a metal, for example silver. Such particles appear relatively neutral as regards the color of the composition.

Reflective particles that may be used in the composition of the present disclosure and have a metallic or white glint may, for example, reflect light in all components of the visible region without significantly absorbing one or more wavelengths. The spectral reflectance of such reflective particles can, for example, be more than 70% in the range 400 nm (nanometers) to 700 nm, and may be at least 80%, or even 90% or 95%.

The light reflected by the reflective particles need not be iridescent, such as when the glint is metallic.

Regardless of their form, the reflective particles may optionally have a multilayered structure; in the case of a multi-layered structure, for example, they may have at least one layer of uniform thickness, such as a reflective material.

When the reflective particles do not have a multilayered structure, they may, for example, be composed of metal oxides, such as oxides of titanium or iron obtained by synthesis so that they have a substantially planar surface having a surface state which is not matt, for example, and not diffusing, allowing sufficient specular light reflection to obtain highlight points in the cosmetic composition.

When the reflective particles have a multilayered structure they may, for example, comprise a natural or synthetic substrate, such as a synthetic substrate which is at least partially coated with at least one layer of a reflective material, such as at least one metal or metallic compound. The substrate may be a single material or a multiple materials, organic and/or inorganic, and solid or hollow.

Regardless of the form of the reflective particles, when it is synthetic, the substrate may be produced in a form that encourages the formation of a reflective surface after coating, such as after depositing a layer of reflective material. As an example, the substrate may have a planar surface and the layer of reflective material may have a substantially uniform thickness.

In one embodiment, among the substrates that may be used, non-limiting mention may be made of substrates chosen from glasses, ceramics, graphite, metal oxides, aluminas, silicas, silicates such as aluminosilicates and borosilicates, talc, mica, synthetic mica, metals, and mixtures thereof.

The reflective material may comprise a layer of metal or of a metallic compound.

The layer of metal or of a metallic compound may optionally completely coat the substrate, and the metal layer may be at least partially coated with a layer of another material, for example a transparent material. In one embodiment, the layer of metal or of metallic compound to coat the substrate completely, directly or indirectly, i.e. with the interposition of at least one intermediate layer, which may optionally be metallic.

In one embodiment, the metal may be chosen from Ag, Au, Cu, Al, Ni, Sn, Mg, Cr, Mo, Ti, Pt, Va, Rb, W, Zn, Ge, Te, Se, and mixtures thereof. In a further embodiment, the metal may be chosen from Ag, Au, Al, Zn, Ni, Mo, Cr, Cu, and their alloys (for example bronzes and brasses).

When the particles comprise substrates coated with silver or gold, the metallic layer may be present in an amount ranging from 0.1% to 50% of the total particle weight, such as an amount ranging from 1% to 20%, for example.

Glass particles coated with a metallic layer have been described in Japanese Patent documents JP-A-09188830, JP-A-10158450, JP-A-10158541, JP-A-07258460 and JP-A-05017710, the contents of which are incorporated by reference.

Further examples of reflective particles comprising a mineral substrate coated with a metal layer that may be mentioned are particles comprising a substrate of borosilicate coated with silver, also termed "white nacres."

Glass substrate particles coated with silver in the form of flakes are sold under the trade name MICROGLASS METASHINE REFSX 2025 PS by TOYAL. Glass substrate particles coated with nickel/chromium/molybdenum alloy are sold under the trade name CRYSTAL STAR GF 550, GF 2525 by the same company. Spherical glass substrate particles which may optionally be coated with a metal are sold under the trade name PRIZMALITE MICROSPHERE by PRIZMALITE INDUSTRIES.

Particles of metallic substrate such as aluminum, copper, bronze, in the form of flakes are sold under the trade name STARBRITE by SILBERLINE and under the trade name VISIONAIRE by ECKART.

Reflective particles of any form may also be chosen from particles of synthetic substrate at least partially coated with at least one layer of at least one metallic compound, such as metal oxides chosen from, for example, oxides of titanium, such as $TiO_2$, iron, such as $Fe_2O_3$, tin, and chromium, barium sulfate, and the following compounds: $MgF_2$, $CrF_3$, $ZnS$, $ZnSe$, $SiO_2$, $Al_2O_3$, $MgO$, $Y_2O_3$, $SeO_3$, $SiO$, $HfO_2$, $ZrO_2$, $CeO_2$, $Nb_2O_5$, $Ta_2O_5$, $MoS_2$, and their mixtures or alloys.

Examples of such particles that may be mentioned are particles comprising a substrate of synthetic mica coated with titanium dioxide, or glass particles coated either with brown iron oxide, titanium oxide, tin oxide, or one of their mixtures such as those sold under the trade name REFLECKS® by ENGELHARD.

Pigments from the METASHINE 1080R range sold by NIPPON SHEET GLASS CO. LTD may also be used. These pigments, such as those described in Japanese patent JP 2001-11340, are flakes of C-GLASS glass comprising 65% to 72% of $SiO_2$ coated with a layer of rutile type titanium oxide ($TiO_2$). Such glass pellets have a mean thickness of 1 micrometer (μm) and a mean size of 80 μm, giving a mean size/mean thickness ratio of 80. They have blue, green, yellow, or silvery glints depending on the thickness of the $TiO_2$ layer.

Further mention may be made of particles with dimensions in the range 80 μm to 100 μm, comprising a substrate of synthetic mica (fluorophlogopite) coated with titanium dioxide representing 12% of the total particle weight, sold under the trade name PROMINENCE by NIHON KOKEN.

The reflective particles may also be chosen from particles formed by a stack of at least two layers with different refractive indices.

The at least two layers may be polymeric or metallic in nature, and in one embodiment, they may include at least one polymeric layer.

The reflective particles may be particles deriving from a multi-layer polymeric film.

Such particles are described in International and United States Patents WO 99/36477, U.S. Pat. No. 6,299,979, and U.S. Pat. No. 6,387,498.

Non-limiting mention of materials that may constitute the various layers of the multilayer structure that may be may be made of: polyethylene naphthalate (PEN) and its isomers, for example 2,6-, 1,4-, 1,5-, 2,7- and 2,3-PEN, polyalkylene terephthalates, polyimides, polyetherimides, atactic polystyrenes, polycarbonates, polymethacrylates and alkyl polyacrylates, syndiotactic polystyrene (sPS), syndiotactic poly-alpha-methylstyrenes, syndiotactic polydichlorostyrene, copolymers and mixtures of said polystyrenes, cellulose derivatives, polyalkylenated polymers, fluorinated polymers, chlorinated polymers, polysulfones, polyethersulfones, polyacrylonitriles, polyamides, silicone resins, epoxy resins, polyvinyl acetate, polyether-amides, ionomeric resins, elastomers and polyurethanes. Copolymers may also be used, for example PEN copolymers, or copolymers of 2,6-, 1,4-, 1,5-, 2,7-, and/or 2,3-naphthalene dicarboxylic acid or its esters with (a) terephthalic acid or its esters; (b) isophthalic acid or its esters; (c) phthalic acid or its esters; (d) alkane glycols; (e) cycloalkane glycols (for example cyclohexane dimethanol diol); (f) dicarboxylic alkane acids; and/or (g) cycloalkane dicarboxylic acids, copolymers of polyalkylene terephthalates, and styrene copolymers. Further, each individual layer may include mixtures of two or more of the above polymers or copolymers.

The choice of materials for constituting the various layers of the multilayered structure is clearly made in a manner such that the desired reflective appearance is obtained in the particles so formed.

Reflective particles comprising a stack of at least two layers of polymers are sold by 3M under the trade name MIRROR GLITTER. These particles comprise layers of 2,6-PEN and polymethylmethacrylate in a 80/20 weight ratio. Such particles are described in U.S. Pat. No. 5,825,643.

Nacres

The at least one second coloring agent may comprise nacres.

The term "nacres" means colored particles of any form, which may optionally be iridescent, as produced in the shells of certain mollusks, or which are synthesized, and which exhibit a "pearlescent" coloring effect by optical interference.

Nacres may be chosen from nacre pigments such as mica titanium coated with iron oxide, mica coated with bismuth oxychloride, mica titanium coated with chromium oxide, mica titanium coated with an organic colorant of the type mentioned, above, and nacre pigments based on bismuth oxychloride. They may also be particles of mica on the surface of which at least two successive layers of metal oxides and/or organic coloring substances have been superimposed.

Examples of nacres that may be mentioned are natural mica coated with titanium oxide, iron oxide, natural pigment, or bismuth oxychloride.

Examples of commercially-available nacres that may be mentioned are the nacres TIMICA, FLAMENCO, and DUOCHROME (mica-based) sold by ENGELHARD, TIMIRON nacres sold by MERCK, PRESTIGE mica-based nacres sold by ECKART, and SUNSHINE synthetic mica-based nacres sold by SUN CHEMICAL.

In one embodiment, the nacres may have a yellow, pink, red, bronze, orangey, brown, gold, and/or coppery color or glint.

Illustrative examples of nacres that may be used in the composition of the present disclosure and that may be mentioned are gold color nacres, such as those sold by ENGELHARD under the trade names Brilliant gold 212G (Timica), Gold 222C (Cloisonne), Sparkle gold (Timica), Gold 4504 (Chromalite), and Monarch gold 233X (Cloisonne); bronze nacres, such as those sold by MERCK under the trade names Bronze fine (17384) (Colorona) and Bronze (17353) (Colorona), and by ENGELHARD under the trade name Super bronze (Cloisonne); orange nacres such as those sold by ENGELHARD under the trade names Orange 363C (Cloisonne) and Orange MCR 101 (Cosmica), and by MERCK under the trade names Passion orange (Colorona) and Matte orange (17449) (Microna); brown-tinted nacres sold by ENGELHARD under the trade names Nu-antique copper 340XB (Cloisonne) and Brown CL4509 (Chromalite); nacres with a copper glint sold by ENGELHARD under the trade name Copper 340A (Timica); nacres with a red glint, such as those sold by MERCK under the trade name Sienna fine (17386) (Colorona); nacres with a yellow glint, such as those sold by ENGELHARD under the trade name Yellow (4502) (Chromalite); red tinted nacres with gold glints, such as those sold by ENGELHARD under the trade name Sunstone G012 (Gemtone); pink nacres, such as those sold by ENGELHARD under the trade name Tan opale G005 (Gemtone); black nacres with a gold glint, such as those sold by ENGELHARD under the trade name Nu antique bronze 240 AB (Timica); blue nacres, such as those sold by MERCK under the trade name Matte blue (17433) (Microna); white nacres with silvery glints, such as those sold by MERCK under the trade name Xirona Silver; and orange-pink/green-gold highlight nacres sold by MERCK under the trade names Indian summer (Xirona) and mixtures thereof.

Goniochromatic Coloring Agents

The at least one second coloring agent may comprise at least one gonio-chromatic coloring agent so that when the composition is applied to its surface, it creates a colored base having color that changes with the angle of observation. A goniochromatic coloring agent in the context of the present disclosure allows a color change, also termed a "color flop", to be observed as a function of the angle of observation, which change is greater than that which is encountered with nacres. A single goniochromatic coloring agent may be used for ease of implementation.

The goniochromatic coloring agent may be selected so that it presents a relatively large color change with changing angle of observation.

The goniochromatic coloring agent may thus be selected so that, for a variation in the angle of observation in the range 0° to 80° with illumination at 45°, the color of the cosmetic composition is observed to vary by an amount ΔE of at least 2, as measured in the 1976 CIE (International Commission on Illumination) calorimetric space.

The goniochromatic coloring agent may also be selected so that, for illumination at 45° and for a variation in the angle of observation in the range 0° to 800, the hue angle of the cosmetic composition in the CIE 1976 plane may be observed to vary by an amount Ah of at least 300, such as at least 400, at least 600, or even at least 1000.

The goniochromatic coloring agent may, for example, be chosen from multilayered interference structures and liquid crystal coloring agents.

A multilayered structure may, for example, comprise at least two layers, each layer, independently or otherwise of the other layer(s), being produced, for example, from at least one material chosen from: $MgF_2$, $CeF_3$, $ZnS$, $ZnSe$, $Si$, $SiO_2$, $Ge$, $Te$, $Fe_2O_3$, $Pt$, $Va$, $Al_2O_3$, $MgO$, $Y_2O_3$, $S203$, $SiO$, $HfO_2$, $ZrO_2$, $CeO_2$, $Nb_2O_5$, $Ta_2O_5$, $TiO_2$, $Ag$, $Al$, $Au$, $Cu$, $Rb$, $Ti$, $Ta$, $W$, $Zn$, $MOS_2$, cryolite, alloys, polymers, and combinations thereof.

The multilayered structure may optionally be symmetrical with respect to a central layer as regards the chemical nature of the stacked layers.

Non-limiting examples of symmetrical multilayered interference structures that may be used in compositions of the present disclosure include: Al/SiO$_2$/AVSiO$_2$/Al, pigments with this structure being sold by DUPONT DE NEMOURS; Cr/MgF$_2$/Al/MgF$_2$/Cr, pigments with this structure being sold under the trade name CHROMAFLAIR by FLEX; MoS$_2$/SiO$_2$/Al/SiO$_2$/MoS$_2$; Fe$_2$O$_3$/SiO$_2$/AVSiO$_2$/Fe$_2$O$_3$, and Fe$_2$O$_3$/SiO$_2$/Fe$_2$O$_3$/SiO$_2$/Fe$_2$O$_3$, pigments having these structures being sold under the trade name SICOPEARL by BASF; MoS$_2$/SiO$_2$/mica-oxide/SiO$_2$/MoS$_2$; Fe$_2$O$_3$/SiO$_2$/mica-oxide/SiO$_2$/Fe$_2$O$_3$; TiO$_2$/SiO$_2$/TiO$_2$ and TiO$_2$/Al$_2$O$_3$/TiO$_2$, SnO/TiO$_2$/SiO$_2$/TiO$_2$/SnO; Fe$_2$O$_3$/SiO$_2$/Fe$_2$O$_3$; SnO/mica/TiO$_2$/SiO$_2$/TiO$_2$/mica/SnO, pigments with these structures being sold under the trade name XIRONA by MERCK (Darmstadt). Further examples of such pigments include pigments with a silica/titanium oxide/tin oxide structure sold under the trade name XIRONA MAGIC by MERCK; brown silica/iron oxide structure pigments sold under the trade name XIRONA INDIAN SUMMER by MERCK and pigments with a silica/titanium oxide/mica/tin oxide structure sold under the trade name XIRONA CARRIBEAN BLUE by MERCK. INFINITE COLORS pigments from SHISEIDO can also be mentioned. Depending on the thickness and nature of the various layers, different effects are obtained. Thus, the structure Fe$_2$O$_3$/SiO$_2$/Al/SiO$_2$/Fe$_2$O$_3$ changes from green-gold to gray-red for SiO$_2$ layers of 320 nm to 350 nm; from red to golden for layers of SiO$_2$ from 380 nm to 400 nm; from violet to green for layers of SiO$_2$ of 410 nm to 420 nm; and from copper to red for layers of SiO$_2$ from 430 nm to 440 nm.

In another embodiment of the present disclosure, the goniochromatic coloring agents comprise a multilayered structure comprising alternating polymeric layers, for example of the polyethylene naphthalate and polyethylene terephthalate type. Such agents have been described in WO-A-96/19347 and WO-A-99/36478.

Examples of pigments with a polymeric multilayered structure that may be mentioned are those sold by 3M under the trade name COLOR GLITTER.

Liquid crystal coloring agents comprise, for example, silicones, or cellulose ethers onto which mesomorphic groups have been grafted.

Examples of suitable liquid crystal goniochromatic particles are those sold by CHENIX, and those sold under the trade name HELICONE® HC by WACKER.

The composition may also include dispersed goniochromatic fibers. Such fibers may, for example, be of a size in the range 50 μm to 700 μm, such as 300 μm.

In one embodiment, interference fibers with a multilayered structure can be used. Fibers with a multilayered structure of polymers have been described in EP-A-0 921 217, EP-A-0 686 858, and U.S. Pat. No. 5,472,798. The multilayered structure may comprise at least two layers, each layer, independently or otherwise of the other layer or layers being produced from at least one synthesized polymer. The polymers present in the fibers may have a refractive index of 1.30 to 1.82, preferably of 1.35 to 1.75. In one embodiment, polymers for the fibers are polyesters such as polyethylene terephthalate, polyethylene naphthalate, polycarbonate; acrylic polymers such as polymethylmethacrylate; and polyamides.

Goniochromatic fibers with a bilayered polyethylene terephthalate/nylon-6 structure are sold by TEIJIN under the trade name MORPHOTEX.

Other Components

Solvents

The composition may include at least one aqueous or organic solvent.

When the composition includes one or more organic solvents, the solvents may be present in an amount of 0.1% to 99% by weight relative to the total composition weight.

The amount of the at least one solvent, such as at least one organic solvent, can depend on the nature of the surface onto which the composition is intended to be applied.

In an embodiment where the composition is a nail polish, for example, the organic solvent may be present in the composition in an amount ranging from 30% to 99% by weight, for example, relative to the total composition weight. In a further embodiment, the at least one organic solvent may be present in the composition in an amount ranging from 60% to 90% by weight relative to the total composition weight.

The composition may comprise at least one organic solvent selected from the following list:
  ketones which are liquid at ambient temperature, such as methylethylketone, methylisobutylketone, diisobutylketone, isophorone, cyclohexanone, or acetone;
  alcohols which are liquid at ambient temperature, such as ethanol, isopropanol, diacetone alcohol, 2-butoxyethanol, or cyclohexanol;
  glycols which are liquid at ambient temperature, such as ethylene glycol, propylene glycol, pentylene glycol or glycerol;
  propylene glycol ethers which are liquid at ambient temperature, such as propylene glycol monomethyl ether, the acetate of propylene glycol monomethyl ether, or dipropylene glycol mono n-butyl ether;
  short chain esters (containing a total of 3 to 8 carbon atoms), such as ethyl acetate, methyl acetate, propyl acetate, n-butyl acetate, or isopentyl acetate; and
  alkanes which are liquid at ambient temperature, such as decane, heptane, dodecane, or cyclohexane.

The composition may also comprise water or a mixture of water and hydrophilic organic solvents which are routinely used in cosmetics, such as alcohols, including linear or branched lower monoalcohols containing 2 to 5 carbon atoms, such as ethanol, isopropanol or n-propanol, polyols such as glycerine, diglycerine, propylene glycol, sorbitol, penthylene glycol, or polyethylene glycols. The composition may also contain hydrophilic C$_2$ ethers and C$_2$-C$_4$ aldehydes. The water or mixture of water and hydrophilic organic solvents may be present in the composition in an amount ranging from 0% to 90%, in particular 0.1% to 90% by weight relative to the total composition weight. In one embodiment, the water or mixture of water and hydrophilic organic solvents may be present in the composition in an amount ranging from 0 to 60% by weight relative to the total composition weight. In a further embodiment, the water or mixture of water and hydrophilic organic solvents may be present in the composition in an amount ranging from 0.1% to 60% by weight relative to the total composition weight.

Oily Phase

In an embodiment of the present disclosure where the composition is to be applied to the lips, the composition may include an oily phase and at least one fat that is liquid at ambient temperature (25° C.) and/or a fat that is solid at ambient temperature, such as waxes, pasty fats, gums, and mixtures thereof. The oily phase may also contain lipophilic organic solvents.

The composition may, for example, have a continuous oily phase which may contain less than 5% water, for example less than 1% water relative to its total weight, and it may be in the anhydrous form.

Among examples of fats that are liquid at ambient temperature, usually termed "oils", that may be mentioned include:
hydrocarbon-containing vegetable oils such as liquid fatty acid triglycerides containing 4 to 10 carbon atoms, for example heptanoic or octanoic acid triglycerides, or sunflower, corn, soybean, grapeseed, sesame seed, apricot kernel, macadamia nut, castor, or avocado stone oil, caprylic/capric acid triglycerides, jojoba oil, shea nut butter oil, lanolin, acetylated lanolin; linear or branched hydrocarbons of mineral or synthetic origin, such as paraffin oils and their derivatives, Vaseline, polydecenes, hydrogenated polyisobutene such as Parleam; synthesized esters and ethers, in particular fatty acids such as Purcellin oil, isopropyl myristate, 2-ethylhexyl palmitate, 2-octyidodecyl stearate, 2-octyldodecyl erucate, isostearyl isostearate; hydroxylated esters such as isostearyl lactate, octylhydroxystearate, octyldodecyl hydroxystearate, diisostearylmalate, triisocetyl citrate, fatty alcohol heptanoates, octanoates or decanoates; isononyl isonanoate, isopropyl lanolate, tridecyl trimellilate, diisostearyl malate; polyol esters such as propylene glycol dioctanoate, neopentylglycol diheptanoate, diethyleneglycol diisononanoate; and pentaerythritol esters; fatty alcohols containing 12 to 26 carbon atoms, such as octyldodecanol, 2-butyloctanol, 2-hexyldecanol, 2-undecylpentadecanol or oleic alcohol; partially hydrocarbonated and/or siliconized fluorinated oils; silicone oils such as volatile or non volatile, linear or cyclic polymethylsiloxanes (PDMS) which may be liquid or pasty at ambient temperature, such as cyclomethicones or dimethicones, optionally comprising a phenyl group, such as phenyl trimethicones, phenyltrimethylsiloxydiphenyl siloxanes, diphenylmethyldimethyl-trisiloxanes, diphenyl dimethicones, phenyl dimethicones, polymethylphenylsiloxanes; and mixtures thereof. The oils may be present in an amount ranging from 0.01% to 90% by weight relative to the total composition weight. In one embodiment, the oils may be present in an amount ranging from 0.1% to 85% by weight relative to the total composition weight.

Pasty fats are generally hydrocarbon-containing compounds with a melting point in the range 25° C. to 60° C., such as in the range 30° C. to 45° C. and/or with hardness in the range 0.001 MPa (megapascals) to 0.5 MPa, such as in the range 0.005 MPa to 0.4 MPa, such as lanolins and derivatives thereof.

Waxes may be solid at ambient temperature (25° C.) with a reversible solid/liquid change of state, with a melting point of more than 30° C. and up to 200° C., a hardness of more than 0.5 MPa, and with an anisotropic crystalline organization in the solid state. In one embodiment, the waxes may have a melting point of more than 25° C., such as more than 45° C. The waxes may be hydrocarbon-containing, fluorinated and/or siliconized and may be of animal, mineral, vegetable and/or synthetic origin. Among examples of waxes that may be used, non-limiting mention may be made are beeswax, carnauba wax, candelilla wax, paraffin, microcrystalline waxes, ceresin, and ozokerite; synthetic waxes such as polyethylene or Fischer-Tropsch waxes and silicone waxes such as alkyl or alkoxydimethicone containing 16 to 45 carbon atoms. The composition may contain 0 to 50% by weight of waxes relative to the total composition weight, or even 1% to 30% by weight.

Among gums that may be used, non-limiting mention may be made of high molecular weight polydimethylsiloxanes (PDMS), cellulose gums, and polysaccharides.

Film-Forming Polymer

The composition may also, for example, include a film-forming polymer, such as embodiments wherein the composition is a mascara or a nail polish. The term "film-forming polymer" designates a polymer that can form, by itself or in the presence of an additional film-forming agent, a continuous film that adheres to a surface, such as to keratinous materials.

Among film-forming polymers that may be used in a composition of the present disclosure, non-limiting mention may be made of synthetic polymers of the radical or polycondensate type, natural polymers such as nitrocellulose or cellulose esters, and mixtures thereof.

Radical type film-forming polymers may in comprise vinyl polymers or copolymers, such as acrylic polymers.

Vinyl film-forming polymers may result from polymerizing monomers with an ethylenically unsaturated bond containing at least one acid group and/or esters of said acid monomers and/or amides of said acid monomers, such as $\alpha,\beta$-ethylenically unsaturated carboxylic acids, for example acrylic acid, methacrylic acid, crotonic acid, maleic acid, or itaconic acid.

Vinyl film-forming polymers may also result from homopolymerizing or copolymerizing monomers chosen from vinyl esters such as vinyl acetate, vinyl neodecanoate, vinyl pivalate, vinyl benzoate, and vinyl t-butyl benzoate, and styrene monomers such as styrene and alpha-methyl styrene.

Non-limiting examples of film-forming polycondensates that may be mentioned include polyurethanes, polyesters, polyester amides, polyamides, and polyureas.

Polymers of natural origin, which may optionally be modified, may be chosen from shellac resin, gum sandarac, dammar resin, gum elemi, copal resin, cellulose polymers such as nitrocellulose, ethylcellulose, or nitrocellulose esters selected, for example, from cellulose acetate, cellulose acetobutyrate, and cellulose acetopropionate, and mixtures thereof.

The film-forming polymer may be present in the form of solid particles in an aqueous or oily dispersion, generally known as latexes or psuedolatexes. The film-forming polymer may comprise one or more stable dispersions of generally spherical polymer particles of one or more polymers in a physiologically acceptable liquid oily phase. Such dispersions are generally termed polymer NADs (non aqueous dispersions), in contrast to latexes which are aqueous polymer dispersions. These dispersions may be in the form of nanoparticles of polymers in stable dispersion in said oily phase. The nanoparticle size can be in the range 5 nm to 600 nm. Techniques for preparing said dispersions are well known to the skilled person.

Aqueous film-forming polymer dispersions which may be used are acrylic dispersions sold under the trade names NEOCRYL XK-90®, NEOCRYL A-1070®, NEOCRYL A-1090®, NEOCRYL BT-62®, NEOCRYL A-1079®, NEOCRYL A-523® by AVECIA-NEORESINS, and DOW LATEX 432® by DOW CHEMICAL; DAITOSOL 5000 AD® by DAITO KASEI KOGYO; or aqueous polyurethane dispersions sold under the trade names NEOREZ R-981® and NEOREZ R-974® by AVECIA-NEORESINS; AVALURE UR-405®, AVALURE UR-410®, AVALURE UR-425®, AVALURE UR-450®, SANCURE 875®, SANCURE 861®, SANCURE 878®, and SANCURE 2060® by GOODRICH; IMPRANIL 85® by BAYER; AQUAMERE H-1511® by HYDROMER; and sulfopolyesters sold under the trade mark Eastman AQ by Eastman Chemical Products.

The composition of the present disclosure may also comprise an auxiliary film-forming agent which encourages the formation of a film with the film-forming polymer.

Fillers

The composition may also comprise fillers. The term "fillers" means particles of any form which are insoluble in the composition medium regardless of the temperature at which the composition is manufactured. The fillers primarily act to modify the rheology or texture of the composition. The nature and quantity of the solid substances are a function of the desired mechanical properties and textures.

Examples of fillers that may be mentioned include talc, mica, silica, kaolin, and sericite, and powders of polyamide, polyethylene, polytetrafluoroethylene, polymethylmethacrylate, or polyurethane, powdered starch, and silicone resin beads.

Additional Coloring Substance

The composition may comprise an additional coloring substance which differs from the composite pigment used in the present disclosure.

The additional coloring substance may be selected from mineral pigments, organic pigments and liposoluble or hydrosoluble colorants.

The mineral pigments may be white or colored, and may optionally be coated. The following may be mentioned: titanium dioxide, which may be surface treated; oxides of zirconium or cerium; and oxides of iron or of chromium; manganese violet; ultramarine blue; chromium hydrate; and iron blue. The pigments may be present in an amount ranging from 0% to 40% by weight relative to the total composition weight. In one embodiment, the pigments may be present in an amount ranging from 1% to 35% by weight relative to the total composition weight. In a further embodiment, the pigments may be present in an amount ranging from 2% to 25% by weight of the total composition weight.

Organic pigments that may be mentioned are carbon black, D&C type pigments, and lakes based on carmine cochineal, barium, strontium, calcium, or aluminum.

Non-limiting examples of liposoluble colorants are Sudan red, D&C Red No. 17, D&C Green No. 6, β-carotene, soybean oil, Sudan brown, D&C Yellow No. 11, D&C Violet No. 2, D&C orange No. 5, and quinoline yellow.

Non-limiting examples of hydrosoluble colorants are beetroot juice and methylene blue.

The colorants may be present in the composition an amount ranging from 0.1% to 20% by weight relative to the total weight of the composition, such as from 0.1% to 6% (if present).

Other Ingredients

The composition may include at least one cosmetic or dermatological active ingredient. Examples of cosmetic, dermatological, hygienic, or pharmaceutical active ingredients that may be used in the composition of the present disclosure that may be mentioned are moisturizing agents (polyols such as glycerine), vitamins (C, A, E, F, B, or PP), essential fatty acids, essential oils, ceramides, sphingolipids, liposoluble or nanoparticle sun screens, and specific skin treatment active ingredients (protective agents, antibacterials, anti-wrinkle agents, etc). The active ingredients may, for example, be present in the composition in amounts ranging from 0% to 20% by weight relative to the total composition weight. In one embodiment, the active ingredients may be present in amounts ranging from 0.001% to 15% by weight relative to the total composition weight.

The cosmetic composition may also contain ingredients which are routinely used in cosmetics, such as thickeners, surfactants, oligo-elements, moisturizing agents, softeners, sequestrating agents, fragrances, alkalinizing or acidifying agents, preservatives, antioxidants, UV filters, colorants, or mixtures thereof.

Depending on the envisaged application, the composition of the present disclosure may include constituents which are conventionally used in the fields under consideration, and which are present in quantities appropriate to the desired dosage or "galenical" form.

Galenical Forms

The composition may be in a variety of forms, depending on its destination. The composition may thus be in any galenical form which is normally used for topical application, such as in the anhydrous form, in the form of an oily or aqueous solution, an oily or aqueous gel, an oil-in-water emulsion, a water-in-oil emulsion, a wax-in-water or a water-in-wax emulsion, a multiple emulsion or a dispersion of oil in water due to vesicles located on the oil/water interface.

The composition may be in the form of a cast product, such as a stick in the case of a lipstick or a lip care product.

The composition may also be in a variety of other forms, for example a liquid of greater or lesser viscosity, a gel or a paste.

The composition may also be in solid form, for example a bar to be moistened for use, to allow it to disintegrate.

The cosmetic composition may constitute a makeup composition, including a lipstick, a liquid gloss, a lipstick paste, a blusher, a lip crayon, a solid or fluid foundation, a concealer or eye contour product, an eye liner, a mascara, a nail polish, an eye shadow, a body or hair makeup product, or a sun care product, or skin coloring product.

The present disclosure also provides a lipstick, which may be liquid or solid, comprising a composition as defined above.

The present disclosure also provides a foundation comprising a composition as defined above.

The present disclosure also provides a nail polish comprising a composition as defined above.

The present disclosure also provides a mascara comprising a composition as defined above.

The present disclosure also provides a product for coloring hair fibers and comprising a composition as defined above.

The present disclosure also provides a method of making up the skin, the lips, the nails, or hair in which a composition as defined above is applied to the skin, the lips, the nails, or hair.

The present disclosure is illustrated in more detail by the non-limiting examples described below.

EXAMPLES

By way of illustration, cosmetic compositions comprising first and second coloring agents with the following formulations were produced, the compositions being prepared using conventional cosmetic preparation methods.

Examples 1, 2 and Comparative Example 1

Lipstick

Example 1

A lipstick with the following composition of the present disclosure was prepared (quantities expressed as a % by weight relative to the total composition weight):

| | |
|---|---|
| Polyethylene wax | 10 |
| Octyldodecyl neopentanoate | 47.1 |
| Hydrogenated polybutene | 20 |
| Phenyl trimethylsiloxytrisiloxane | 15 |
| Goniochromatic pigment (SICOPEARL Fantastico Green (BASF)) | 5.5 |
| silica/D&C Red No.7[1] composite pigment | 2.4 |

[1] Composite pigment constituted by 50 parts by weight of D&C Red No. 7 per 100 parts of an organic silica core with a mean size of 15 nm and a specific surface area of 200 m$^2$/g produced with a polymethylhydrogen siloxane binder.

Example 2

A lipstick with the following composition of the present disclosure was prepared (quantities expressed as a % by weight relative to the total composition weight):

| | |
|---|---|
| Polyethylene wax | 10 |
| Octyldodecyl neopentanoate | 47.1 |
| Hydrogenated polybutene | 20 |
| Phenyl trimethylsiloxy trisiloxane | 15 |
| Goniochromatic pigment (SICOPEARL Fantastico Green (BASF)) | 5.5 |
| $TiO_2$/D&C Red No.7[2] composite pigment | 2.4 |

[2]Composite pigment constituted by 50 parts by weight of D&C Red No.7 per 100 parts of an inorganic core of titanium dioxide with a mean size of 20 nm and a specific surface area of 50 $m^2$/g produced with a polymethylhydrogen siloxane binder.

Comparative Example 1

A lipstick was prepared with the following composition, not in accordance with the present disclosure as it contained no composite pigment (quantities expressed as a % by weight relative to the total composition weight):

| | |
|---|---|
| Polyethylene wax | 10 |
| Octyldodecyl neopentanoate | 48.7 |
| Hydrogenated polybutene | 20 |
| Phenyl trimethylsiloxytrisiloxane | 15 |
| Goniochromatic pigment (SICOPEARL Fantastico Green (BASF)) | 5.5 |
| D&C Red No.7[3] organic pigment | 0.8 |

[3]Organic pigment denominated D&C Red No.7.

The lipsticks of Examples 1, 2 and Comparative Example 1 were deposited using an automatic spreader onto the black background of a type 24/5 ERICSEN contrast card comprising a black background and a white background, with a thickness of 100 μm.

The color path of the various samples in the a*b* plane of the 1976 CIE calorimetric space was then measured in reflection using a NIPPON DENSHOKU KOGYO GC-5000 spectrogoniocolorimeter with an angle of incidence of 45° and an angle of observation of 0 to 70°.

| Angle of observation (°) | Example 1 a* | Example 1 b* | Example 2 a* | Example 2 b* | Comparative Example 1 a* | Comparative Example 1 b* |
|---|---|---|---|---|---|---|
| 0 | 12.8 | 5.2 | 16.5 | 3.9 | 14.3 | 7.2 |
| 10 | 13.5 | 2.8 | 17.4 | 2.0 | 13.8 | 4.1 |
| 20 | 14.9 | −0.8 | 18.7 | −0.8 | 14.8 | 0.3 |
| 30 | 16.7 | −3.6 | 20.3 | −3.6 | 16.0 | −3.1 |
| 40 | 5.1 | −2.0 | 9.2 | −5.9 | 4.8 | −3.3 |
| 50 | −16.6 | −13.0 | −19.7 | −14.6 | 1.5 | −4.8 |
| 60 | 17.3 | −2.3 | 21.3 | −2.5 | 18.3 | −2.9 |
| 70 | 19.6 | 1.1 | 20.0 | 1.1 | 19.2 | 0.5 |

Comparative example 1 did not show the green component of the pigment and had a reduced "color flop" effect compared with that of Examples 1 and 2.

Example 3

Liquid Foundation

A liquid foundation in accordance with the present disclosure may be prepared with the following composition (quantities expressed as a % by weight relative to the total composition weight):

| | |
|---|---|
| Dimethicone copolyol | 5 |
| Dimethicone | 4 |
| Cyclomethicone | 15 |
| Isododecane | 10 |
| Bentone gel | 10 |
| Nylon powder | 2 |
| PMMA powder | 2 |
| Yellow iron oxide | 4 |
| $TiO_2$/D&C Red No.7 composite pigment | 1 |
| Mica/bismuth oxychloride/brown iron oxide[4] pigment | 5 |
| Water | 31.2 |
| Butylene glycol | 10 |
| Magnesium sulfate | 0.8 |

[4]Chroma-Lite Brown sold by ENGELHARD.

Example 4

Nail Polish

A nail polish in accordance with the present disclosure may be prepared with the following composition (quantities expressed as a % by weight relative to the total composition weight):

| | |
|---|---|
| Nitrocellulose | 19 |
| N-ethyl-o,p-toluene sulfonamide | 6 |
| Acetyl tributyl citrate | 6 |
| Rheological agent (hectorite) | 1.2 |
| Silica/D&C Red No7 composite pigment | 3 |
| Silver-coated glass particles[5] | 6 |
| Isopropanol | 8 |
| Ethyl acetate/butyl acetate | qsp 100 |

[5]Metashine REFSX 2040 PS sold by TOYAL.

A sparkle effect linked to the presence of the silver-coated glass particles may be observed.

Clearly, the present disclosure is not limited to the examples given above.

Throughout the description, including in the claims, the expression "comprising a" should be understood as being synonymous with "comprising at least one", unless stated otherwise.

The ranges given should be construed as including their limits, unless stated otherwise.

Although the present disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

What is claimed is:

1. A composition for application to the skin, the lips, the nails, and/or hair, said composition comprising:
    at least one first coloring agent in an amount sufficient to color the composition, comprising particles of at least one non-interference composite pigment, said particles comprising an inorganic core at least partially coated with at least one organic coloring substance, and at least one binder, and wherein the inorganic core comprises $TiO_2$; and
    at least one second coloring agent in an amount sufficient to produce a specific optical effect in the composition which is visibly perceptible to a human observer; and further wherein the mean size of the inorganic core ranges from 1 nm to 100 nm.

2. The composition according to claim 1, wherein the specific optical effect is a point highlight effect.

3. The composition according to claim 1, wherein the specific optical effect is a goniochromatic effect.

4. The composition according to claim 1, wherein the specific optical effect is a speckled effect.

5. The composition according to claim 1, wherein the at least one first coloring agent is present in the composition in an amount ranging from 0.1% to 20% by weight relative to the total composition weight.

6. The composition according to claim 5, wherein the at least one first coloring agent is present in the composition in an amount ranging from 0.1% to 10% by weight relative to the total composition weight.

7. The composition according to claim 6, wherein the at least one first coloring agent is present in the composition in an amount ranging from 0.5% to 5% by weight relative to the total composition weight.

8. The composition according to claim 1, wherein the at least one second coloring agent is present in an amount ranging from 0.1% to 50% by weight relative to the total composition weight.

9. The composition according to claim 8, wherein the at least one second coloring agent is present in the composition in and amount ranging from 0.5% to 40% by weight relative to the total composition weight.

10. The composition according to claim 9, wherein the at least one second coloring agent is present in the composition in an amount ranging from 1% to 20% by weight relative to the total composition weight.

11. The composition according to claim 1, wherein the weight ratio of the at least one second coloring agent to the at least one first coloring agent ranges from 0.1 to 50.

12. The composition according to claim 11, wherein the weight ratio of the at least one second coloring agent to the at least one first coloring agent ranges from 0.5 to 30.

13. The composition according to claim 12, wherein the weight ratio of the at least one second coloring agent to the at least one first coloring agent ranges from 1 to 10.

14. The composition according to claim 1, wherein the at least one organic coloring substance comprises at least one organic pigment.

15. The composition according to claim 1, wherein the at least one organic coloring substance comprises at least one organic lake.

16. The composition according to claim 1, wherein the mean size of the inorganic core ranges from 5 nm to 75 nm.

17. The composition according to claim 16, wherein the mean size of the inorganic core ranges from 10 nm to 50 nm.

18. The composition according to claim 1, wherein the specific surface area of the inorganic core ranges from 1 $m^2/g$ to 1000 $m^2/g$.

19. The composition according to claim 18, wherein the specific surface area of the inorganic core ranges from 10 $m^2/g$ to 600 $m^2/g$.

20. The composition according to claim 19, wherein the specific surface area of the inorganic core ranges from 20 $m^2/g$ to 400 $m^2/g$.

21. The composition according to claim 1, wherein the inorganic core further comprises at least one additional material chosen from metallic salts, metal oxides other than $TiO_2$, alumina, glass, ceramics, graphite, silica, silicates, and synthetic micas.

22. The composition according to claim 21, wherein the metal oxide oxides other than $TiO_2$ are chosen from oxides of iron, cerium, zirconium, zinc, aluminum, iron blue, and chromium.

23. The composition according to claim 22, wherein the metal oxides other than $TiO_2$ are chosen from oxides of iron, cerium, zirconium, zinc, and aluminum.

24. The composition according to claim 23, wherein the mean size of the inorganic core ranges from 10 nm to 50 nm.

25. The composition according to claim 21, wherein the inorganic core further comprises at least one silicate chosen from an aluminosilicate and a borosilicate.

26. The composition according to claim 21, wherein the inorganic core further comprises silica.

27. The composition according to claim 1, wherein the proportion by weight of the at least one organic coloring substance ranges from 10 to 500 parts by weight per 100 parts by weight of inorganic core.

28. The composition according to claim 27, wherein the proportion by weight of the at least one organic coloring substance ranges from 20 to 250 parts by weight per 100 parts by weight of inorganic core.

29. The composition according to claim 28, wherein the proportion by weight of the at least one organic coloring substance ranges from 40 to 125 parts by weight per 100 parts by weight of inorganic core.

30. The composition according to claim 1, wherein the at least one organic coloring substance is chosen from carmine cochineal, organic pigments of azo, anthraquinone, indigo, xanthene, pyrene, quinoline, triphenylmethane, and fluorane dyes, organic lakes, insoluble sodium, potassium, calcium, barium, aluminum, zirconium, strontium, and titanium organic salts, and acid dyes.

31. The composition according to claim 30, wherein the at least one acid dye is chosen from azo, anthraquinone, indigo, xanthene, pyrene, quinoline, triphenyl-methane, and fluorane dyes, and dyes comprising at least one carboxylic acid group or sulfonic acid group.

32. The composition according to claim 1, wherein the at least one organic coloring substance comprises an organic lake supported by an organic support comprising at least one colophane or aluminum benzoate.

33. The composition according to claim 1, wherein the at least one organic coloring substance comprises an organic pigment chosen from D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, and FD&C Yellow No. 6.

34. The composition according to claim 1, wherein the at least one organic coloring substance comprises an organic lake chosen from D&C Red No. 2 Aluminum lake, D&C Red No. 3 Aluminum lake, D&C Red No. 4 Aluminum lake, D&C Red No. 6 Aluminum lake, D&C Red No. 6 Barium lake, D&C Red No. 6 Barium/Strontium lake, D&C Red No. 6 Strontium lake, D&C Red No. 6 Potassium lake, D&C Red No. 7 Aluminum lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminum lake, D&C Red No. 9 Barium lake, D&C Red No. 9 Barium/Strontium lake, D&C Red No. 9 Zirconium lake, D&C Red No. 10 Sodium lake, D&C Red No. 19 Aluminum lake, D&C Red No. 19 Barium lake, D&C Red No. 19 Zirconium lake, D&C Red No. 21 Aluminum lake, D&C Red No. 21 Zirconium lake, D&C Red No. 22 Aluminum lake, D&C Red No. 27 Aluminum lake, D&C Red No. 27 Aluminum/Titanium/Zirconium lake, D&C Red No. 27 Barium lake, D&C Red No. 27 Calcium lake, D&C Red No. 27 Zirconium lake, D&C Red No. 28 Aluminum lake, D&C Red No. 30 lake, D&C Red No. 31 Calcium lake, D&C Red No. 33 Aluminum lake, D&C Red No. 34 Calcium lake, D&C Red No. 36 lake, D&C Red No. 40 Aluminum lake, D&C Blue No. 1 Aluminum lake, D&C Green No. 3 Aluminum lake, D&C Orange No. 4 Aluminum lake, D&C Orange No. 5 Aluminum lake, D&C Orange No. 5 Zirconium lake, D&C Orange No. 10 Aluminum lake, D&C Orange No. 17 Barium lake, D&C Yellow No. 5 Aluminum lake, D&C Yellow No. 5 Zirconium lake, D&C Yellow No. 6 Aluminum lake, D&C Yellow No. 7 Zirconium lake, D&C Yellow No. 10 Aluminum lake, FD&C Blue No. 1 Aluminum lake, FD&C Red No. 4 Aluminum lake, FD&C Red No. 40 Aluminum lake, FD&C Yellow No. 5 Aluminum lake, and FD&C Yellow No. 6 Aluminum lake.

35. The composition according to claim 1, wherein the at least one binder comprises at least one compound chosen from silicone compounds, polymeric compounds, oligomeric compounds comprising at least one organosilane, organosilanes of fluoroalkylated organosilanes, polysiloxanes, and coupling agents.

36. The composition according to claim 35, wherein the at least one coupling agent is based on at lease one compound chosen from a silane, a titanate, an aluminate, and a zirconate.

37. The composition according to claim 1, wherein the at least one binder is organic.

38. The composition according to claim 35, wherein the at least one binder comprises at least one silicone compound.

39. The composition according to claim 35, wherein the at least one binder comprises polymethylhydrogen siloxane.

40. The composition according to claim 1, wherein the inorganic core is colored.

41. The composition according to claim 1, wherein said composition does not comprise uncoated particles of titanium dioxide.

42. The composition according to claim 1, wherein the at least one second coloring agent comprises particles in the form of flakes.

43. The composition according to claim 1, wherein the at least one second coloring agent comprises particles having a globular form.

44. The composition according to claim 1, wherein the at least one second coloring agent has a multilayered structure.

45. The composition according to claim 44, wherein the at least one second coloring agent comprises a substrate chosen from at least one of a metal, a metal oxide, and a polymer.

46. The composition according to claim 1, wherein the at least one second coloring agent comprises nacres.

47. The composition according to claim 46, wherein the at least one second coloring agent comprises at least one a compound chosen from mica, a synthetic mica, a talc, a silica, and an alumina.

48. The composition according to claim 1, wherein the at least one second coloring agent comprises glass-based particles.

49. The composition according to claim 1, wherein the at least one second coloring agent comprises surface-metallized particles.

50. The composition according to claim 1, wherein the at least one second coloring agent comprises metal particles chosen from aluminum, bronze, copper, and alloys thereof.

51. The composition according to claim 1, wherein the at least one second coloring agent comprises reflective particles.

52. The composition according to claim 51, wherein the reflective particles comprise particles comprise a natural or synthetic substrate at least partially coated with at least one layer of at least one metal or metallic compound.

53. The composition according to claim 52, wherein the substrate is chosen from single material substrates, multimaterial substrates, organic substrates, and inorganic substrates.

54. The composition according to claim 53, wherein the substrate is chosen from glasses, ceramics, graphite, metal oxides, aluminas, silicas, silicates, talc, mica, synthetic mica, metals, and mixtures thereof.

55. The composition according to claim 54, wherein the substrate is chosen from aluminosilicates and borosilicates.

56. The composition according to claim 55, wherein the metallic compound is chosen from titanium oxides, iron oxides, tin oxides, chromium oxides, barium sulfate, $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$, and mixtures or alloys thereof.

57. The composition according to claim 56, wherein the metallic compound is $Fe_2O_3$.

58. The composition according to claim 51, wherein the metal is chosen from Ag, Au, Cu, Al, Zn, Ni, Mo, Cr, and mixtures or alloys thereof.

59. The composition according to claim 51, wherein the reflective particles are at least partially comprised of particles formed by a stack of at least two layers with different refractive indices.

60. The composition according to claim 59, wherein the at least two layers with different refractive indices comprise two layers of polymers.

61. The composition according to claim 1, wherein the at least one second coloring agent comprises at least one goniochromatic coloring agent.

62. The composition according to claim 61, wherein the at least one goniochromatic coloring agent is chosen from liquid crystal coloring agents and multilayered interference structures.

63. The composition according to claim 62, wherein the at least one goniochromatic coloring agent comprises a multilayered interference structure chosen from $Al/SiO_2/Al/SiO_2/Al$; $Cr/MgF_2/Al/MgF_2/Cr$; $MoS_2/SiO_2/Al/SiO_2/MoS_2$; $Fe_2O_3/SiO_2/Al/SiO_2/Fe_2O_3$; $Fe_2O_3/SiO_2/Fe_2O_3/SiO_2/Fe_2O_3$; $MoS_2/SiO_2/mica-oxide/SiO_2/MoS_2$; $Fe_2O_3/SiO_2/mica-oxide/SiO_2/Fe_2O_3$; $TiO_2/SiO_2/TiO_2$; $TiO_2/Al_2O_3/TiO_2$; $SnO/TiO_2/SiO_2/TiO_2/SnO$; $Fe_2O_3/SiO_2/Fe_2O_3$; and $SnO/mica/TiO_2/SiO_2/TiO_2/mica/SnO$.

64. The composition according to claim 1, further comprising an additional coloring substance that differs from the at least one composite pigment.

65. The composition according to claim 64, wherein the additional coloring substance is chosen from mineral pigments, organic pigments, liposoluble colorants, and hydrosoluble colorants.

66. The composition according to claim 1, wherein the saturation C* of the composite pigment is greater than about 30.

67. A composition for application to the skin, the lips, the nails, and/or hair, said composition comprising:
- at least one first coloring agent in an amount sufficient to color the composition, comprising particles of at least one composite pigment, said particles comprising an inorganic core at least partially coated with at least one organic coloring substance, and at least one binder, and wherein the inorganic core comprises $TiO_2$; and
- at least one second coloring agent in an amount sufficient to produce a specific optical effect in the composition which is visibly perceptible to a human observer, wherein the mean size of the inorganic core ranges from 1 nm to 100 nm.

68. The composition according to claim 67, wherein the mean size of the inorganic core ranges from 10 nm to 50 nm.

69. The composition according to claim 68, wherein the BET specific surface area of the inorganic core ranges from 20 $m^2/g$ to 400 $m^2/g$.

70. The composition according to claim 67, wherein the at least one binder comprises at least one silicone compound.

71. The composition according to claim 67, wherein the at least one organic coloring substance is different from melanin.

72. The composition according to claim 67, wherein the weight of proportion of the binder is less than 5% relative to the total weight of the composite pigment.

* * * * *

UNITED STATES PATENT AND TRADEMARK OFFICE
CERTIFICATE OF CORRECTION

| | | |
|---|---|---|
| PATENT NO. | : 7,981,404 B2 | Page 1 of 1 |
| APPLICATION NO. | : 11/100513 | |
| DATED | : July 19, 2011 | |
| INVENTOR(S) | : Christophe Dumousseaux | |

It is certified that error appears in the above-identified patent and that said Letters Patent is hereby corrected as shown below:

Claim 36, column 25, line 42, "at lease one compound" should read -- at least one compound --

Signed and Sealed this
Fifteenth Day of November, 2011

David J. Kappos
*Director of the United States Patent and Trademark Office*